(12) United States Patent
Tiberg et al.

(10) Patent No.: US 9,555,118 B2
(45) Date of Patent: *Jan. 31, 2017

(54) ROBUST CONTROLLED-RELEASE PEPTIDE FORMULATIONS

(71) Applicant: CAMURUS AB, Lund (SE)

(72) Inventors: Fredrik Tiberg, Lund (SE); Markus Johnsson, Lund (SE)

(73) Assignee: CAMRUS AB (SE)

(*) Notice: Subject to any disclaimer, the term of this patent is extended or adjusted under 35 U.S.C. 154(b) by 0 days.

This patent is subject to a terminal disclaimer.

(21) Appl. No.: 14/362,542

(22) PCT Filed: Nov. 28, 2012

(86) PCT No.: PCT/EP2012/073841
§ 371 (c)(1),
(2) Date: Jun. 3, 2014

(87) PCT Pub. No.: WO2013/083459
PCT Pub. Date: Jun. 13, 2013

(65) Prior Publication Data
US 2014/0329749 A1    Nov. 6, 2014

Related U.S. Application Data

(60) Provisional application No. 61/566,851, filed on Dec. 5, 2011.

(51) Int. Cl.

| | | |
|---|---|---|
| *A61K 9/20* | (2006.01) | |
| *A61K 47/24* | (2006.01) | |
| *A61K 9/00* | (2006.01) | |
| *A61K 47/10* | (2006.01) | |
| *A61K 47/14* | (2006.01) | |
| *A61K 9/107* | (2006.01) | |
| *A61K 9/127* | (2006.01) | |
| *A61K 38/12* | (2006.01) | |
| *A61K 31/485* | (2006.01) | |
| *A61K 38/08* | (2006.01) | |
| *A61K 38/09* | (2006.01) | |

(52) U.S. Cl.
CPC ............ *A61K 47/24* (2013.01); *A61K 9/0024* (2013.01); *A61K 9/1075* (2013.01); *A61K 9/1274* (2013.01); *A61K 31/485* (2013.01); *A61K 38/08* (2013.01); *A61K 38/09* (2013.01); *A61K 38/12* (2013.01); *A61K 47/10* (2013.01); *A61K 47/14* (2013.01)

(58) Field of Classification Search
CPC .... A61K 9/0024; A61K 9/1274; A61K 47/10; A61K 47/14; A61K 47/24; A61K 38/09; A61K 38/08
See application file for complete search history.

(56) References Cited

U.S. PATENT DOCUMENTS

| | | | |
|---|---|---|---|
| 4,938,763 A | | 7/1990 | Dunn et al. |
| 5,151,272 A | | 9/1992 | Engstrom et al. |
| 5,480,656 A | | 1/1996 | Okada et al. |
| 5,538,739 A | | 7/1996 | Bodmer et al. |
| 5,807,573 A | * | 9/1998 | Ljusberg-Wahren ............... A61K 9/1274 424/450 |
| 5,955,502 A | * | 9/1999 | Hansen ............... A61K 9/0014 424/407 |
| 6,113,943 A | | 9/2000 | Okada et al. |
| 6,464,987 B1 | * | 10/2002 | Fanara ............... A61K 9/0019 424/400 |
| 6,630,115 B1 | | 10/2003 | Kaneeda et al. |
| 7,473,761 B2 | | 1/2009 | Albert et al. |

(Continued)

FOREIGN PATENT DOCUMENTS

| | | |
|---|---|---|
| WO | 2005/039642 A1 | 5/2005 |
| WO | 2005/046642 A1 | 5/2005 |

(Continued)

OTHER PUBLICATIONS

International Search Report in Application No. PCT/EP2012/073841 dated Jun. 13, 2013.
International Report on Patentability in Application No. PCT/EP2012/073841 dated Jun. 10, 2014.
A. Bradford et al.: "The Effect of Vitamin E on the Structure of Membrane Lipid Assemblies," Journal of Lipid Research, vol. 44, pp. 1940-1945, Jul. 16, 2003.
S. Leikin et al.: "Measured Effects of Diacylglycerol on Structural and Elastic Properties of Phospholipid Membranes," Biophysical Journal, vol. 71, pp. 2623-2632, Nov. 1996.

(Continued)

*Primary Examiner* — Snigdha Maewall
(74) *Attorney, Agent, or Firm* — J.A. Lindeman & Co. PLLC

(57) ABSTRACT

The present invention relates to compositions forming a low viscosity mixture of: a. 25-55 wt. % of at least one diacyl glycerol and/or at least one tocopherol; b. 25-55 wt. % of at least one phospholipid component comprising phospholipids having i. polar head groups comprising more than 50% phosphatidyl ethanolamine, and ii. two acyl chains each independently having 16 to 20 carbons wherein at least one acyl chain has at least one unsaturation in the carbon chain, and there are no more than four unsaturations over two carbon chains; c. 5-25 wt. % of at least one biocompatible, oxygen containing, low viscosity organic solvent; wherein 0.1-10 wt. % of at least one peptide active agent comprising at least one somatostatin receptor agonist is dissolved or dispersed in the low viscosity mixture; and wherein the pre-formulation forms, or is capable of forming, at least one non-lamellar liquid crystalline phase structure upon contact with an aqueous fluid. The invention further relates to methods of treatment comprising administration of such compositions, and to pre-filled administration devices and kits containing the formulations.

36 Claims, 10 Drawing Sheets

(56) References Cited

U.S. PATENT DOCUMENTS

2005/0014686 A1  1/2005  Albert et al.

FOREIGN PATENT DOCUMENTS

| WO | 2005/070392 A2 | 8/2005 |
| WO | 2005/070394 A2 | 8/2005 |
| WO | 2005/117830 A1 | 12/2005 |
| WO | 2006/075123 A1 | 7/2006 |
| WO | 2006/075124 A1 | 7/2006 |
| WO | 2006/077362 A1 | 7/2006 |
| WO | 2006/131730 A1 | 12/2006 |
| WO | 2008/152401 A1 | 12/2008 |

OTHER PUBLICATIONS

Nilesh Patel et al.: "Phospholipid-based Microemulsions Suitable for Use in Foods," Journal of Agricultural and Food Chemistry, vol. 54, No. 20, pp. 7817-7824, Oct. 2006.

S.W.J. Lamberts et al.: "New Somatostatin Analogs: Will they Fulfil Old Promises?" European Journal of Endocrinology, vol. 146, No. 5, pp. 701-705, Jan. 1, 2002.

* cited by examiner

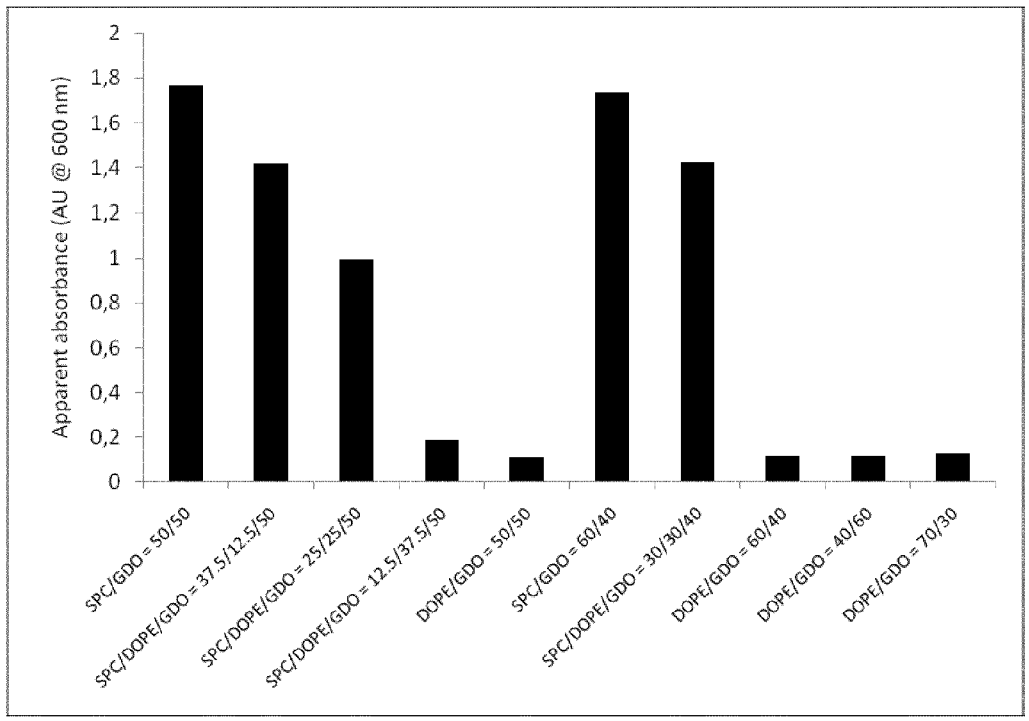
Figure 1: Apparent absorbance (turbidity) of the aqueous phase measured at 600 nm for gels with the indicated lipid compositions (wt%) incubated in 0.1 wt% sodium taurocholate (NaTC). The gels were incubated at 37°C for 6 hours with moderate shaking (150 rpm). See also Table 1 for composition details.

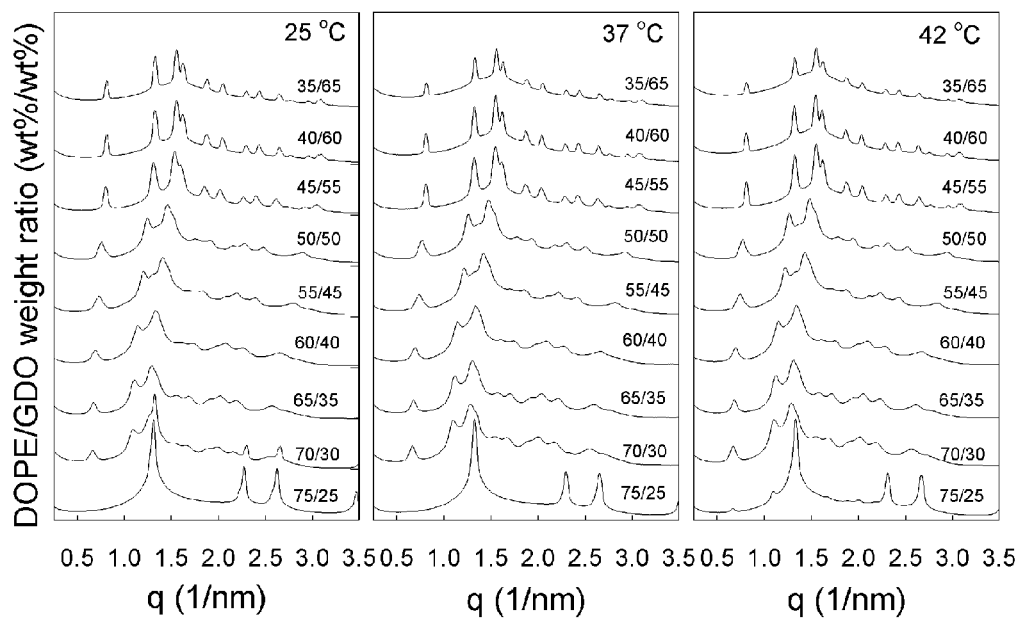
Figure 2. X-ray diffraction patterns of fully hydrated DOPE/GDO mixtures in saline at 25, 37 and 42°C between DOPE/GDO weight ratios of 75/25 and 35/65 as indicated in the figure. The relative diffraction peak positions indicate the liquid crystalline structure change from reversed hexagonal to reversed micellar cubic (space group Fd3m) when the GDO content is increased.

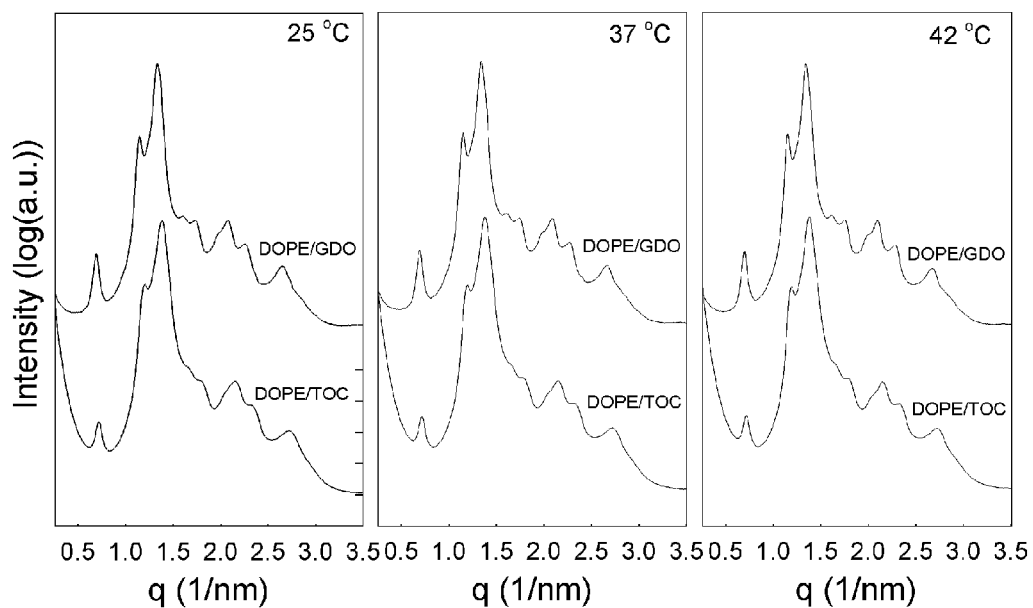
Figure 3. X-ray diffraction patterns of fully hydrated DOPE/GDO (60/40 by weight) and DOPE/TOC (60/40 by weight) mixtures in saline at 25, 37 and 42°C. The relative diffraction peak positions indicate the same reversed micellar cubic (Fd3m) liquid crystalline structure within the temperature range investigated.

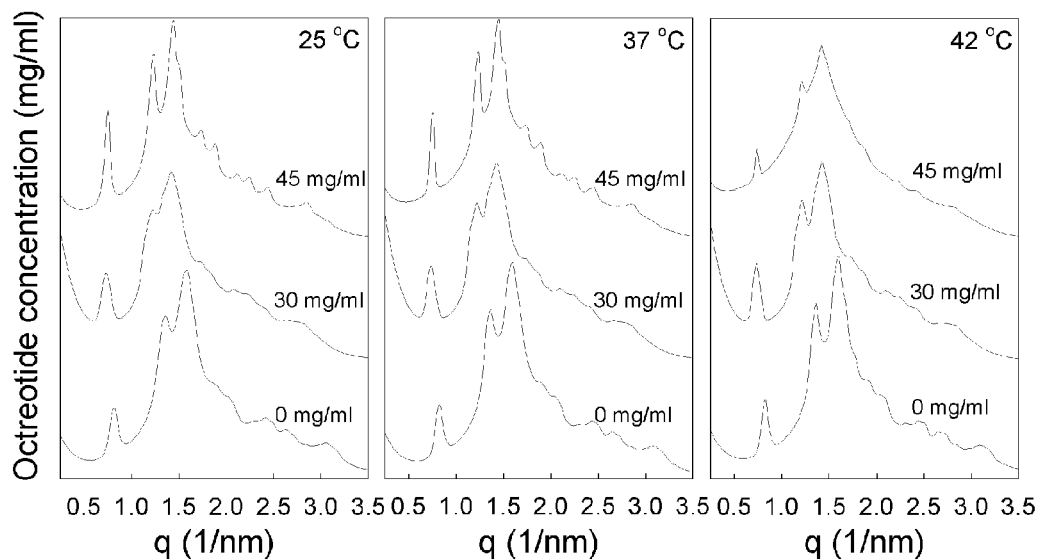

Figure 4. X-ray diffraction patterns of fully hydrated (in saline (0.9% NaCl w/v)) DOPE/GDO (50/50 by weight) mixtures including octreotide at 25, 37 and 42°C. The octreotide concentration in the respective lipid formulation is indicated in the figure. The relative diffraction peak positions indicate the same reversed micellar cubic (Fd3m) liquid crystalline structure within the octreotide concentration and temperature range investigated.

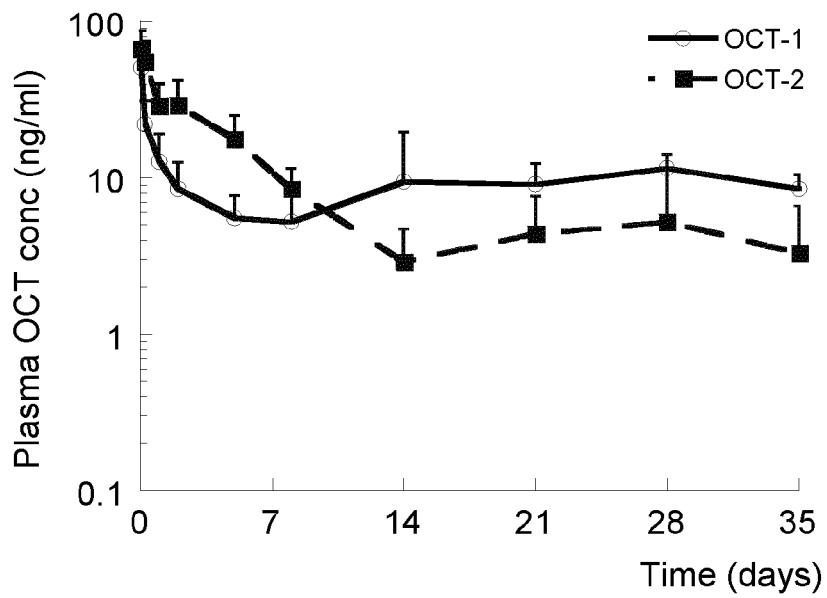
Figure 5. In vivo pharmacokinetic profile of octreotide (OCT) after subcutaneous administration in rats. Error bars denote standard deviation (n = 6). Formulation compositions are provided in Example 10.

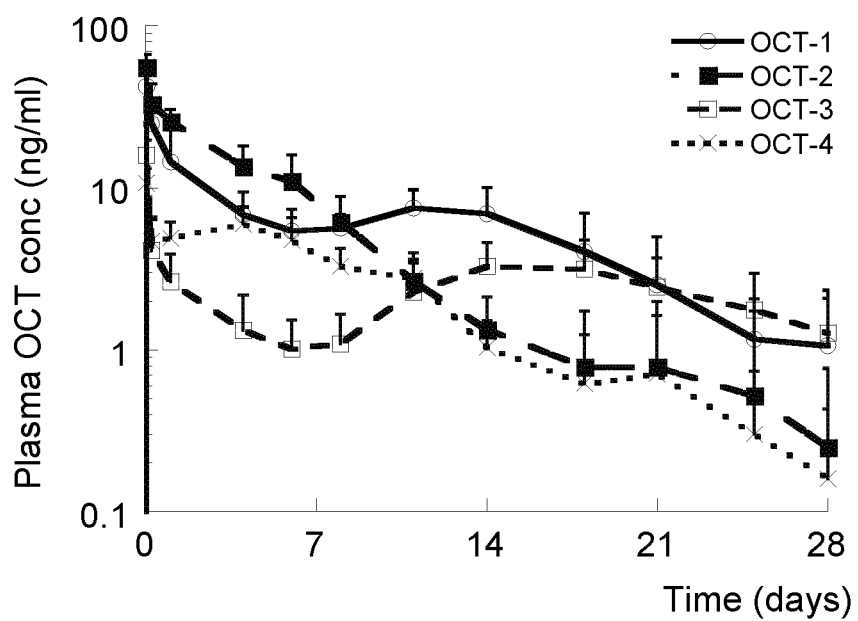
Figure 6. In vivo pharmacokinetic profile of octreotide (OCT) after subcutaneous administration in rats. Error bars denote standard deviation (n = 6). Formulation compositions are provided in Example 11.

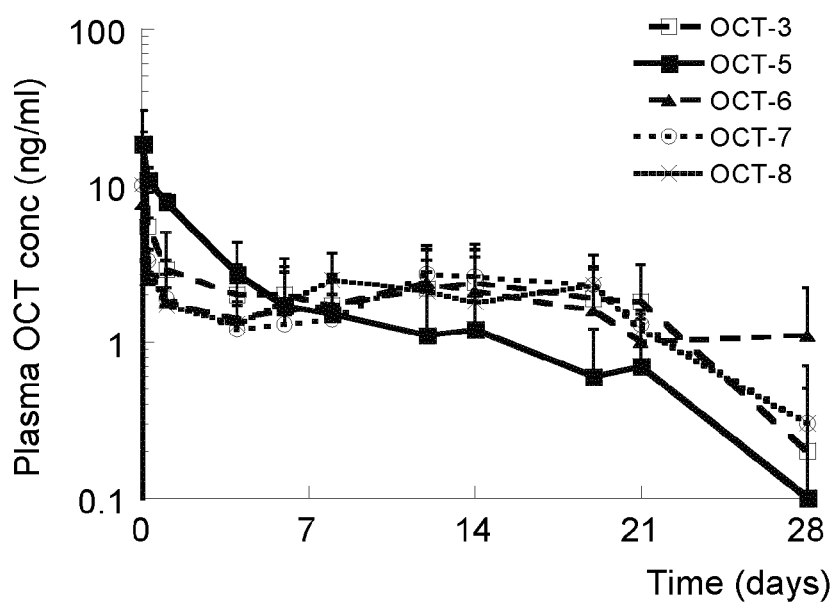
Figure 7. In vivo pharmacokinetic profile of octreotide (OCT) after subcutaneous administration in rats. Error bars denote standard deviation (n = 6). Formulation compositions are provided in Example 12.

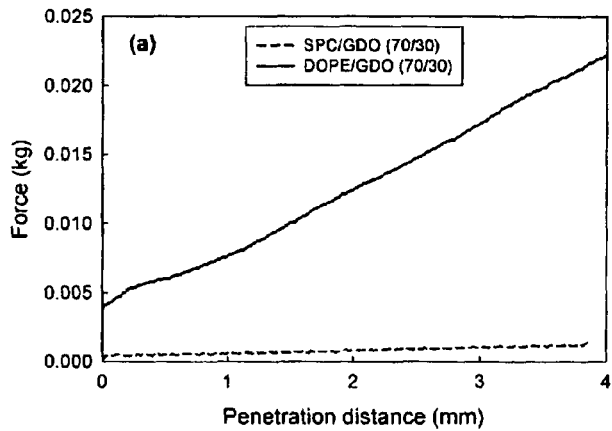

Figure 8(a). A comparison of the mechanical robustness of liquid crystalline gels formed by DOPE/GDO and SPC/GDO mixtures in aqueous solution (PBS, pH 7.4). The following phospholipid/GDO weight ratios were investigated and compared: 70:30.

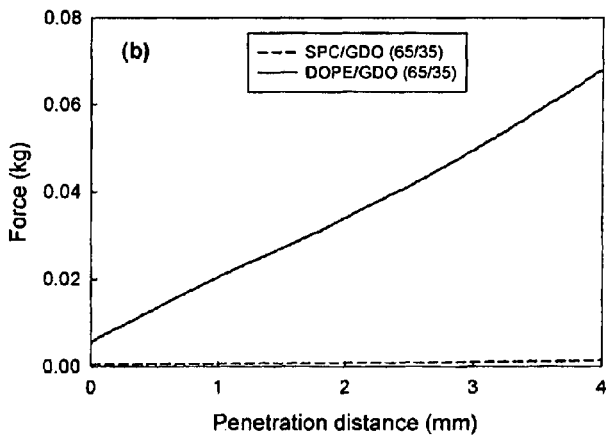

Figure 8(b). A comparison of the mechanical robustness of liquid crystalline gels formed by DOPE/GDO and SPC/GDO mixtures in aqueous solution (PBS, pH 7.4). The following phospholipid/GDO weight ratios were investigated and compared: 65:35.

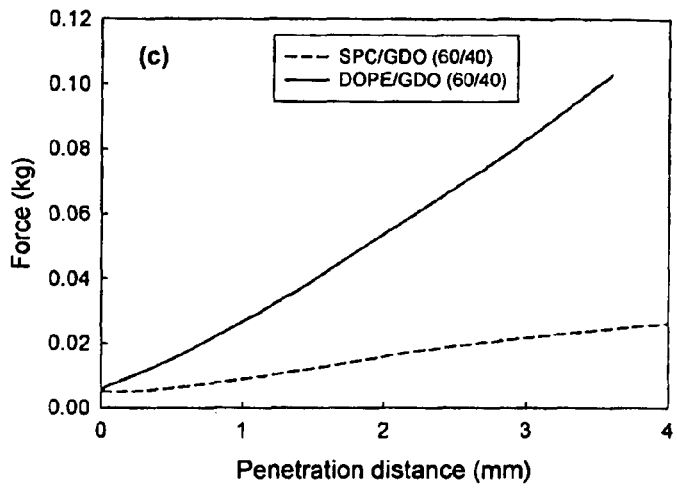

Figure 8(c). A comparison of the mechanical robustness of liquid crystalline gels formed by DOPE/GDO and SPC/GDO mixtures in aqueous solution (PBS, pH 7.4). The following phospholipid/GDO weight ratios were investigated and compared: 60:40.

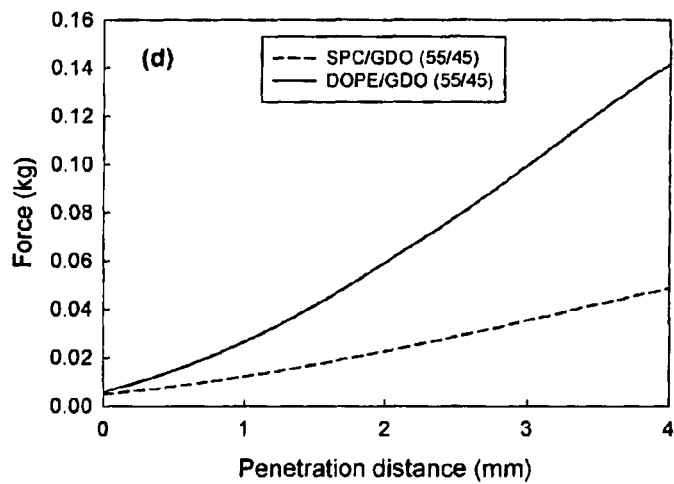

Figure 8(d). A comparison of the mechanical robustness of liquid crystalline gels formed by DOPE/GDO and SPC/GDO mixtures in aqueous solution (PBS, pH 7.4). The following phospholipid/GDO weight ratios were investigated and compared: 55:45.

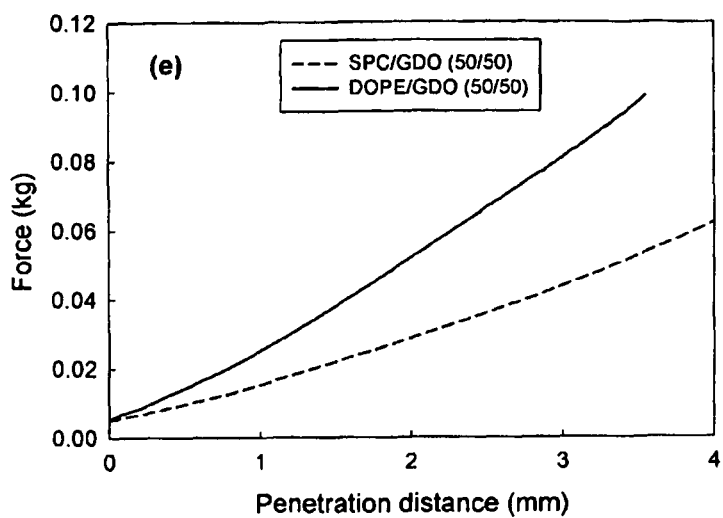
Figure 8(e). A comparison of the mechanical robustness of liquid crystalline gels formed by DOPE/GDO and SPC/GDO mixtures in aqueous solution (PBS, pH 7.4). The following phospholipid/GDO weight ratios were investigated and compared: 50:50.

ROBUST CONTROLLED-RELEASE PEPTIDE FORMULATIONS

FIELD

The present invention relates to formulation precursors (pre-formulations) comprising lipids that upon exposure to water or aqueous media, such as body fluids, spontaneously undergo at least one phase transition, thereby forming a controlled release matrix which optionally is bioadhesive.

BACKGROUND

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable. Furthermore, in some circumstances, such as in the fitting of implants (e.g. joint replacements or oral implants) the area of desired action may not remain accessible for repeated administration. In such cases a single administration must provide active agent at a therapeutic level over the whole period during which activity is needed.

Sustained activity is furthermore important in situations where a physical soothing or barrier property is provided by a formulation. In such circumstances the biological effect may be provided by, for example, the separation of a biological tissue from some undesirable agent or environment or by the provision of a soothing interface between the tissue and its surroundings. Where compositions provide such a barrier or interfacial property, whether including a "drug" type active agent or not, it is an advantage if the composition is sufficiently permanent to allow a reasonable period between administrations.

Different methods have been used and proposed for the sustained release of biologically active agents. Such methods include slow-release, orally administered compositions, such as coated tablets, formulations designed for gradual absorption, such as transdermal patches, and slow-release implants such as "sticks" implanted under the skin.

One method by which the gradual release of a bioactive agent has been proposed is a so-called "depot" injection. In this method, a bioactive agent is formulated with carriers providing a gradual release of active agent over a period of a number of hours, days, weeks, or even months. These are often based upon a degrading matrix which gradually degrades and/or disperses in the body to release the active agent.

There is an enormous potential in the use of peptides (including proteins) for treating various disease states, as well as in prophylaxis and in improving general health and well-being of subjects. However, the performance of administered peptide agents is generally limited due to poor bioavailability, which in turn is caused by the rapid degradation of peptides and proteins in biological fluids. This increases the dose which must be administered and in many cases restricts the effective routes of administration. These effects are further exaggerated by the often limited permeability of peptides and proteins across biological membranes.

Peptides and proteins that are administered to the mammalian body (e.g. orally, intramuscularly etc.) are subject to degradation by various proteolytic enzymes and systems present throughout the body. Well known sites of peptidase activity include the stomach (e.g. pepsin), and the intestinal tract (e.g. trypsin, chymotrypsin, and others) but other peptidases (e.g. aminopeptidases, carboxypeptidases, etc.) are found throughout the body. Upon oral administration, gastric and intestinal degradation reduces the amount of peptide or protein which potentially could be absorbed through the intestinal surface lining and thereby decreases their bioavailability. Similarly, free peptides and proteins in the mammalian blood stream are also subject to enzymatic degradation (e.g. by plasma proteases etc.).

Some patients undergoing treatment will typically require a therapeutic dose to be maintained for a considerable period and/or ongoing treatment for many months or years. Thus a depot system allowing loading and controlled release of a larger dose over a longer period would offer a considerable advantage over conventional delivery systems.

The most common of the established methods of depot injection relies upon a polymeric depot system. This is typically a biodegradable polymer such as poly (lactic acid) (PLA) and/or poly (lactic-co-glycolic acid) (PLGA) and may be in the form of a solution in an organic solvent, a pre-polymer mixed with an initiator, encapsulated polymer particles or polymer microspheres. The polymer or polymer particles entrap the active agent and are gradually degraded releasing the agent by slow diffusion and/or as the matrix is absorbed. Examples of such systems include those described in U.S. Pat. No. 4,938,763, U.S. Pat. No. 5,480,656 and U.S. Pat. No. 6,113,943 and can result in delivery of active agents over a period of up to several months. These systems do, however, have a number of limitations including the complexity of manufacturing and difficulty in sterilising (especially the microspheres). The local irritation caused by the lactic and/or glycolic acid which is released at the injection site is also a noticeable drawback. There is also often quite a complex procedure to prepare the injection dose from the powder precursor requiring reconstitution of the system before administration to a subject e.g. by injection.

Peptides may be delivered by systems such as the Alkermes Medisorb® delivery system consisting of microspheres of biodegradable polymers. Such polymer microsphere formulations must generally be administered by means of a sizable needle, typically of 20-gauge or wider. This is necessary as a result of the nature of the polymeric dosing systems used, which are typically polymer suspensions.

Evidently, it would be an advantage to provide a system of low viscosity, such as a homogeneous solution, dispersion of fine particles, or $L_2$ phase, which could be administered easily through a narrow needle, thus decreasing the discomfort of the patient during the procedure. This ease of administration is particularly significant where patients will be on a self-administration regime and may already be self-administering several times each day. Providing a sustained formulation with a duration of a few days, but which is sufficiently complex to administer that it requires treatment by a healthcare professional will not be an advantage to all patients over twice-daily or daily self-administration, and is likely to be more costly. Providing a formulation which gives sufficiently long duration to justify a visit to a health professional for administration and/or a preparation which can be self-administered, and reducing preparation time of health-care professionals or patients prior to the actual administration are all important issues.

From a drug delivery point of view, polymer depot compositions also have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, then drop back through the bottom of the functional window during the lag period before reaching a sustained functional concentration. Evidently, from a functional and toxicological point of view this burst/lag release profile is undesirable and could be dangerous. It may also limit the equilibrium concentration which can be provided due to the danger of adverse effects at the "peak" point.

One class of peptide hormones which benefits particularly from a very "low burst", stable in vivo concentration are Somatostatin receptor agonists such as Pasireotide (SOM230). In vivo testing suggests that these peptides are particularly beneficial when maintained at a steady plasma concentration and as a regulatory hormone, somatostatin and its analogues are particularly likely to benefit from a stable plasma level. This not only suggests that a depot composition would be an advantage to avoid "spikes" in concentration upon administration and/or repeated daily dosing, but furthermore that such a depot composition should have as flat a release profile as possible during the therapeutic period.

Controlled-release formulations are typically generated from bio-compatible polymers in the form of, for example, implants or injectable beads. The current leading formulation of Pasireotide, for example (Pasireotide LAR) comprises microparticles of poly (D,L-lactide-co-glycolide). There is a corresponding formulation for octreotide. Polymer microsphere formulations must generally be administered by means of a sizable needle, typically of 20-gauge or wider. This is necessary as a result of the nature of the polymeric dosing systems used, which are typically polymer suspensions. It would be an advantage to provide a system of low viscosity, such as a homogeneous solution, dispersion of fine particles, or $L_2$ phase, which could be administered easily through a narrow needle, thus decreasing the discomfort of the patient during the procedure. Ease of administration is particularly significant when patients will be self-administering but also reduces the burden on healthcare professionals when they are conducting the administration.

Previous depot systems have been sought to address the problem of burst release. In particular, the use of hydrolysed polylactic acid and the inclusion of poly lactic acid-polyethylene glycol block copolymers have been proposed to provide the "low burst" polymeric system described in U.S. Pat. No. 6,113,943 and U.S. Pat. No. 6,630,115. These systems provide improved profiles but the burst/lag effect remains and they do not address other issues such as the irritation caused by the use of polymers producing acidic degradation products.

One alternative to the more established, polymer based, depot systems is to use a lipid-based slow release matrix comprising a liquid crystalline phase. Systems of this type have been proposed, for example, in U.S. Pat. No. 5,151,272, and WO2005/117830. Such compositions have many advantages and are potentially highly effective, but in some situations it can be an advantage to have lipid based compositions that are even longer lasting, more resistant to chemical and/or enzymatic degradation and/or more physically robust than those proposed in the known literature.

The formation of non-lamellar phases in certain regions of the amphiphile (e.g. lipid)/water, amphiphile/oil and amphiphile/oil/water phase diagrams is a well known phenomenon. Such phases include non-lamellar liquid crystalline phases such as the cubic P, cubic D, cubic G, cubic micellar and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon the mean curvature of the amphiphile sheets or layers, these phases may be described as normal (mean curvature towards the apolar region) or reversed (mean curvature towards the polar region).

Knowledge of the spontaneous or preferred curvature of a particular component allows some degree of prediction as to which structures will be formed or formable by that amphiphile in aqueous mixtures. However, particularly where mixtures of amphiphiles is concerned, the exact nature of the phase structure and physical properties of the composition will depend greatly upon the specific interaction between the components with each other and/or with the solvent and other components of the mixtures.

The non-lamellar liquid crystalline and L3 phases formed by certain amphiphiles and mixtures thereof are thermodynamically stable systems. That is to say, they are not simply a meta-stable state that will separate and/or reform into layers, lamellar phases or the like, but are the stable thermodynamic form of the lipid/solvent mixture.

The early attempts to develop lipid depot formulations, as in, for example, U.S. Pat. No. 5,151,272 and U.S. Pat. No. 5,807,573, using liquid crystal phases could in some cases be effective in terms of delivery but their performance was less than ideal in other critical properties. In particular, cubic liquid crystalline phases are relatively viscous in nature. This makes application with a standard syringe difficult, and possibly painful to the patient, and makes sterilisation by filtration impossible because the composition cannot be passed through the necessary fine-pored membrane.

WO2005/117830, for example, provides an improved system which has low viscosity so as to improve the ease of manufacturing, handling and administration with a standard syringe, allow for sterile filtration and reduce the pain on injection to the patient. However, for long-term depot formulations and/or for formulations having protective or soothing properties (such as surface-coating formulations for use in, for example, per-oral applications), a crucial property is related to the robustness of the gel formed by the pre-formulation in the presence of e.g. aqueous body fluids towards chemical and/or mechanical degradation, e.g. erosion/fragmentation/dissolution by endogenous surface active agents (surfactants), lipid-degrading enzymes and/or physical break-up.

The present inventors have now established that providing a pre-formulation comprising particular amphiphilic components, a biologically tolerable solvent and at least one peptide active agent comprising at least one somatostatin receptor agonist, especially in a low viscosity phase such as molecular solution, gives a pre-formulation with greatly improved mechanical and/or chemical/enzymatic robustness. In addition, the pre-formulation maintains many or all of the advantages of previous lipid depot systems, i.e. it is easy to manufacture, may be sterile-filtered, it has low viscosity (allowing easy and less painful administration), allows a high level of peptide active agent to be incorporated (thus allowing a smaller amount of composition to be used) and/or forms a desired non-lamellar depot composition in vivo having a controllable "burst" or "non-burst" release profile. Advantages in terms of the protective and/or soothing nature of the compositions may also be maintained. The compositions are also formed from materials that are non-toxic, biotolerable and biodegradable.

Due to its improved resistance to degradation from erosion and/or fragmentation by physical and/or chemical means, the pre-formulation is especially suitable for the formation of depot compositions following parenteral administration for long-term drug delivery, e.g. several days to several months after parenteral administration. The compositions are also advantageous for non-parenteral (e.g. local or topical) administration to body cavities and/or surfaces of the body or elsewhere.

In particular, the compositions of the current invention are more resistant to chemical/biological degradation and their mechanical resistance is improved in comparison with existing lipid depot systems, while retaining the ability to spontaneously self-assemble in situ. When tested in degradative/fragmenting systems which cause turbidity upon breakup of the depot, the turbidity factor of the present formulations has been demonstrated as being a factor of ten lower than for the previous lipid based liquid crystal forming systems. This makes the compositions of the invention particularly effective in terms of the longevity of release. They are also well suited for application in areas with high erosion/degradation problems, for example per-oral application, or lower-GI-tract applications.

A lipid-based, slow-release composition based upon phosphatidyl choline and other lipid components is described in WO2006/131730 for GLP-1 and analogues thereof. This is a highly effective formulation, but the concentration of active agent which can be included in the formulation is limited by its solubility. Evidently, a higher concentration of active agent, together with improved mechanical and/or chemical/enzymatic robustness allows for the possibility of even longer duration depot products, products maintaining a higher systemic concentration, and products having a smaller injection volume, all of which factors are of considerable advantage under appropriate circumstances. It would thus be of considerable value to establish a way by which higher concentrations of active agents could be included in a lipid-based depot formulation.

The present inventors have now further established that by incorporating at least one polar solvent a pre-formulation may be generated addressing many of the shortfalls of known depot formulations, and which may be applied to provide an improved controlled release of a peptide active agent comprising at least one somatostatin receptor agonist. By use of specific components in carefully selected ratios, and in particular with a mixture of an alcohol and a polar solvent, a robust depot formulation can be generated having a combination of properties exceeding the performance of even the known lipid controlled-release compositions.

SUMMARY OF THE INVENTION

Viewed from a first aspect, the invention thus provides a pre-formulation comprising a low viscosity, non-liquid crystalline, mixture of:
  a. 25-55 wt. % of at least one diacyl glycerol and/or at least one tocopherol;
  b. 25-55 wt. % of at least one phospholipid component comprising phospholipids having
    i. polar head groups comprising more than 50% phosphatidyl ethanolamine, and
    ii. two acyl chains each independently having 16 to 20 carbons wherein at least one acyl chain has at least one unsaturation in the carbon chain, and there are no more than four unsaturations over the two carbon chains;
  c. 5-25 wt. % of at least one biocompatible, oxygen containing, low viscosity organic solvent;
wherein 0.1-10 wt. % of at least one peptide active agent comprising at least one somatostatin receptor agonist is dissolved or dispersed in the low viscosity mixture; and wherein the pre-formulation forms, or is capable of forming, at least one non-lamellar (e.g. non-lamellar liquid crystalline) phase structure upon contact with an aqueous fluid.

Generally, the aqueous fluid will be a body fluid such as fluid from a mucosal surface, tears, sweat, saliva, gastrointestinal fluid, extra-vascular fluid, extracellular fluid, interstitial fluid or plasma, and the pre-formulation will form a liquid crystalline phase structure when contacted with a body surface, area or cavity (e.g. in vivo) upon contact with the aqueous body fluid. The pre-formulation of the invention may optionally contain a certain amount of water prior to administration, but this will not be sufficient to lead to the formation of the necessary liquid crystalline phase.

Thus in one embodiment applicable to all aspects of the invention, the pre-formulation further comprises:
  d. 1 to 20 wt. % of at least one polar solvent by weight of components a)+b)+c)+d), preferably wherein said polar solvent has a dielectric constant of at least 28 measured at 25° C., more preferably at least 30 measured at 25° C.

In a second aspect the invention provides a method of delivery of a peptide active agent comprising at least one somatostatin receptor agonist to a human or non-human animal (preferably mammalian) body, this method comprising administering a pre-formulation comprising a non-liquid crystalline, low viscosity mixture of:
  a. 25-55 wt. % of at least one diacyl glycerol and/or at least one tocopherol;
  b. 25-55 wt. % of at least one phospholipid component comprising phospholipids having
    i. polar head groups comprising more than 50% phosphatidyl ethanolamine, and
    ii. two acyl chains each independently having 16 to 20 carbons wherein at least one acyl chain has at least one unsaturation in the carbon chain, and there are no more than four unsaturations over the two carbon chains;
  c. 5-25 wt. % of at least one biocompatible, oxygen containing, low viscosity organic solvent;
and 0.1-10 wt. % of at least one peptide active agent comprising at least one somatostatin receptor agonist is dissolved or dispersed in the low viscosity mixture, whereby to form at least one non-lamellar liquid crystalline phase structure upon contact with an aqueous fluid in vivo following administration.

The method of administration suitable for the above method of the invention will be a method appropriate for the condition to be treated and the peptide active agent used. A parenteral depot will thus be formed by parenteral (e.g. subcutaneous or intramuscular) administration while a bioadhesive non-parenteral (e.g. topical) depot composition may be formed by administration to the surface of skin, mucous membranes and/or nails, to ophthalmological, nasal, oral or internal surfaces or to cavities such as oral, nasal, rectal, vaginal or buccal cavities, the periodontal pocket or cavities formed following extraction of a natural or implanted structure or prior to insertion of an implant (e.g. a joint, stent, cosmetic implant, tooth, tooth filling or other implant).

Viewed from a further aspect, the invention provides a method for the preparation of a liquid crystalline composition comprising exposing a pre-formulation comprising a non-liquid crystalline, low viscosity mixture of:

a. 25-55 wt. % of at least one diacyl glycerol and/or at least one tocopherol;
b. 25-55 wt. % of at least one phospholipid component comprising phospholipids having
   i. polar head groups comprising more than 50% phosphatidyl ethanolamine, and
   ii. two acyl chains each independently having 16 to 20 carbons wherein at least one acyl chain has at least one unsaturation in the carbon chain, and there are no more than four unsaturations over the two carbon chains;
c. 5-25 wt. % of at least one biocompatible, oxygen containing, low viscosity organic solvent;

and 0.1-10 wt. % of at least one peptide active agent comprising at least one somatostatin receptor agonist dissolved or dispersed in the low viscosity mixture, to an aqueous fluid in vivo.

The liquid crystalline composition formed in this method may be bioadhesive as described herein. A further aspect of the invention thus resides in the generation of a bioadhesive formulation by administration of any of the formulation precursors (pre-formulations) indicated herein to a body surface, such as any of those body surfaces indicated herein. The increased robustness of the composition of the invention makes it particularly suitable for administration of active agents over an increased duration. In addition the composition demonstrates improved erosion-resistance which further increases the duration of administration enabling e.g. once monthly or once every three months (once quarterly) injections. In particular, because the formulations of the present invention show most unusual and surprising resistance to degradation by digestive systems, such as bile acids, a further highly advantageous application of the present pre-formulations is in per-oral administration where other depot type systems are unsuitable. Parenteral and per-oral methods of administration are thus most preferred for this composition.

Viewed from yet another aspect, the invention provides a process for the formation of a pre-formulation suitable for the administration of a peptide active agent to a (preferably mammalian) subject, said process comprising forming a non-liquid crystalline, low viscosity mixture of a. 25-55 wt. % of at least one diacyl glycerol and/or at least one tocopherol;
b. 25-55 wt. % of at least one phospholipid component comprising phospholipids having
   i. polar head groups comprising more than 50% phosphatidyl ethanolamine, and
   ii. two acyl chains each independently having 16 to 20 carbons wherein at least one acyl chain has at least one unsaturation in the carbon chain, and there are no more than four unsaturations over the two carbon chains;
c. 5-25 wt. % of at least one biocompatible, oxygen containing, low viscosity organic solvent;

and dissolving or dispersing 0.1-10 wt. % of at least one peptide active agent comprising at least one somatostatin receptor agonist in the low viscosity mixture, or in at least one of components a, b or c prior to forming the low viscosity mixture.

Methods for the formation of pre-formulations of the present invention will preferably comprise the mixing of components a), b) and c) (and d) if present), as these components are described herein. Such a mixing method may in one embodiment comprise the mixing of components a) and b) prior to the addition of component c). Alternatively or additionally, the mixing of components a), b) and c) may comprise heating of a mixture of these components to a temperature above 24° C. (e.g. 25 to 50° C.) for a suitable period (e.g. for 1 to 24 hours). Such a method will preferably take place under conditions such that a clear homogeneous mixture of a single phase is generated.

Viewed from another aspect the invention further provides the use of a non-liquid crystalline, low viscosity mixture of:

a. 25-55 wt. % of at least one diacyl glycerol and/or at least one tocopherol;
b. 25-55 wt. % of at least one phospholipid component comprising phospholipids having
   i. polar head groups comprising more than 50% phosphatidyl ethanolamine, and
   ii. two acyl chains each independently having 16 to 20 carbons wherein at least one acyl chain has at least one unsaturation in the carbon chain, and there are no more than four unsaturations over the two carbon chains;
c. 5-25 wt. % of at least one biocompatible, oxygen containing, low viscosity organic solvent;

wherein 0.1-10 wt. % of at least one peptide active agent comprising at least one somatostatin receptor agonist is dissolved or dispersed in the low viscosity mixture, in the manufacture of a pre-formulation for use in the sustained administration of said active agent, wherein said pre-formulation is capable of forming at least one non-lamellar liquid crystalline phase structure upon contact with an aqueous fluid.

Such a use may be in the manufacture of a medicament for use in the treatment, prevention and/or palliation of any condition indicated herein.

In yet a further aspect the invention provides a method of treatment or prophylaxis of a human or non-human (preferably mammalian) animal subject comprising administration of a pre-formulation according to the first aspect of the invention.

In a corresponding aspect, the present invention provides for a pre-formulation as described in any embodiment herein for use in therapy, such as for use in any of those therapies described herein. Thus the pre-formations may be used in the treatment, prevention and/or palliation of any condition indicated herein.

The pre-formulations of the present invention are highly advantageous in that they are stable to prolonged storage in their final "administration ready" form. As a result, they may readily be supplied for administration either by health professionals or by patients or their carers, who need not be fully trained health professionals and may not have the experience or skills to make up preparations following complex reconstitution schemes/instructions.

In a yet further aspect, the present invention provides a disposable administration device (which is also to include a device component) pre-loaded with one or more than one measured dose of a pre-formulation of the present invention. Such a device will, in one embodiment, typically contain a single dose ready for administration and will generally be sterile-packed such that the composition is stored within the device until administration. Such an embodiment is particularly suited to the depot aspects of the invention and is very much suited to the parenteral depot aspects. Suitable devices include cartridges, ampoules and particularly syringes and syringe barrels, either with integral needles or with standard (e.g. luer) fittings adapted to take a suitable disposable needle. In an alternative embodiment, the device may contain a plurality of doses or administrations (e.g. 2 to 100 doses or administrations) of the pre-formulation. Such an embodiment is particularly suited to aspects of the present invention where non-parenteral (e.g. topical) formulations (especially bioadhesive formulations) are generated.

In an additional aspect, the present invention thus provides a disposable administration device pre-loaded with at least one measured dose of a pre-formulation comprising a low viscosity mixture of:
 a. 25-55 wt. % of at least one diacyl glycerol and/or at least one tocopherol;
 b. 25-55 wt. % of at least one phospholipid component comprising phospholipids having
  i. polar head groups comprising more than 50% phosphatidyl ethanolamine, and
  ii. two acyl chains each independently having 16 to 20 carbons wherein at least one acyl chain has at least one unsaturation in the carbon chain, and there are no more than four unsaturations over the two carbon chains;
 c. 5-25 wt. % of at least one biocompatible, oxygen containing, low viscosity organic solvent;
where 0.1 to 10 wt. % of at least one peptide active agent comprising at least one somatostatin receptor agonist is dissolved or dispersed in the low viscosity mixture, and wherein the pre-formulation forms, or is capable of forming, at least one non-lamellar liquid crystalline phase structure upon contact with an aqueous fluid.

The pre-filled devices of the invention may also suitably be included in an administration kit, which kit also forms a further aspect of the invention. In a still further aspect, the invention thus provides a kit for the administration of at least one peptide active agent comprising at least one somatostatin receptor agonist, said kit containing a measured dose of a pre-formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as describe herein and/or for the treatment of a disease indicated herein above.

In a yet further aspect, the invention thus additionally provides a kit for the administration of at least one somatostatin receptor agonist, said kit containing a measured dose of a formulation comprising a low viscosity mixture of:
 a. 25-55 wt. % of at least one diacyl glycerol and/or at least one tocopherol;
 b. 25-55 wt. % of at least one phospholipid component comprising phospholipids having
  i. polar head groups comprising more than 50% phosphatidyl ethanolamine, and
  ii. two acyl chains each independently having 16 to 20 carbons wherein at least one acyl chain has at least one unsaturation in the carbon chain, and there are no more than four unsaturations over the two carbon chains;
 c. 5-25 wt. % of at least one biocompatible, oxygen containing, low viscosity organic solvent;
wherein 0.1-10 wt. % of at least one peptide active agent comprising at least one somatostatin receptor agonist is dissolved or dispersed in the low viscosity mixture, and wherein the pre-formulation forms, or is capable of forming, at least one non-lamellar liquid crystalline phase structure upon contact with an aqueous fluid.

DETAILED DESCRIPTION

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a 22 awg (or a 23 gauge) needle by manual pressure. In a particularly preferred embodiment, the low viscosity mixture should be a mixture capable of passing through a standard sterile filtration membrane such as a 0.22 μm syringe filter. In other preferred embodiments, a similar functional definition of a suitable viscosity can be defined as the viscosity of a pre-formulation that can be sprayed using a compression pump or pressurized spray device using conventional spray equipment. A typical range of suitable viscosities would be, for example, 0.1 to 5000 mPas. The viscosity is preferably 1 to 1000 mPas, more preferably 1 to 800 mPas, such as 50 to 750 mPas, and most preferably 50 to 500 mPas at 20° C.

It has been observed that by the addition of small amounts of low viscosity solvent, as indicated herein, a very significant change in viscosity can be provided. For example, the addition of only 5% solvent can reduce viscosity 100-fold and addition of 10% may reduce the viscosity up to 10,000 fold. In order to achieve this non-linear, synergistic effect, in lowering viscosity it is important that a solvent of appropriately low viscosity and suitable polarity be employed. Such solvents include those described herein infra.

The solvents employed in the pre-formulation of the invention must be biocompatible. In particular, it is preferred if the solvents used are non-halogenated, in particular, non-chlorinated solvents. Preferably halogenated solvents, especially chlorinated solvents are excluded from the pre-formulation of the invention. Thus, in one embodiment, the pre-formulations of all aspects of the invention do not contain any significant amount of halogenated solvent. Thus for example, the amount of halogenated solvent may be below 1 wt % (e.g. 0 to 1 wt %) of the total weight of pre-formulation. This will preferably be less than 0.5%, more preferably less than 0.1% and more preferably less than 0.01% by weight.

Where percentages or ratios are specified herein, these will be by weight unless otherwise specified or context requires otherwise. Generally the percentages will be relative to a specified set of components, such as % of the total weight of components a), b) and c). However, where no other basis is specified, percentages will be by weight of the total precursor formulation (pre-formulation).

Particularly preferred examples of low viscosity mixtures are molecular solutions and/or isotropic phases such as $L_2$ and/or $L_3$ phases. As described above, the $L_3$ is a non-lamellar phase of interconnected sheets which has some phase structure but lacks the long-range order of a liquid crystalline phase. Unlike liquid crystalline phases, which are generally highly viscous, $L_3$ phases are of lower viscosity. Obviously, mixtures of $L_3$ phase and molecular solution and/or particles of $L_3$ phase suspended in a bulk molecular solution of one or more components are also suitable. The $L_2$ phase is the so-called "reversed micellar" phase or microemulsion. Most preferred low viscosity mixtures are molecular solutions, $L_3$ phases and mixtures thereof. $L_2$ phases are less preferred, except in the case of swollen $L_2$ phases as described below.

The present invention provides a pre-formulation comprising components a, b, c and at least one peptide active agent comprising at least one somatostatin receptor agonist as indicated herein. One of the considerable advantages of the pre-formulations of the invention is that components a and b may be formulated in a range of proportions. In particular, it is possible to prepare and use pre-formulations of the present invention having a much greater proportion of phospholipid component b) to diacyl glycerol and/or tocopherol without risking phase separation and/or unacceptably high viscosities in the pre-formulation. The weight ratios of components a:b may thus be anything from around 70:30 to 30:70 (e.g. 68.75:31.25 to 31.25:68.75). Preferably the ratios are in the range from 40:60 to 60:40. Most preferably the ratios are in the range from 45:55 to 55:45, for example 48:52 to 52:48, especially around 50:50.

In one preferred embodiment of the invention, there is a greater proportion of component b than component a. That is, the weight ratio a:b is below 50:50, e.g. 50:50 to 5:95, preferably, 48:52 to 20:80 and more preferably 45:55 to 30:70.

The amount of component c in the pre-formulations of the invention will be at least sufficient to provide a low viscosity mixture (e.g. a molecular solution, see above) of components a, b and c and will be easily determined for any particular combination of components by standard methods. The phase behaviour itself may be analysed by techniques such as visual observation in combination with polarized light microscopy, nuclear magnetic resonance, X-ray diffraction and cryo-transmission electron microscopy (cryo-TEM) to look for solutions, $L_2$ or $L_3$ phases, or liquid crystalline phases. Viscosity may be measured directly by standard means. As described above, an appropriate practical viscosity is that which can effectively be syringed and particularly sterile filtered. This will be assessed easily as indicated herein. The maximum amount of component c to be included will depend upon the exact application of the pre-formulation but generally the desired properties will be provided by any amount forming a low viscosity mixture (e.g. a molecular solution, see above) and/or a solution with sufficiently low viscosity. Since the administration of unnecessarily large amounts of solvent to a subject is generally undesirable the amount of component c will typically be limited to no more than ten times (e.g. three times) the minimum amount required to form a low viscosity mixture, preferably no more than five times and most preferably no more than twice this amount. The composition of the present invention may, however, contain a greater quantity of solvent than would be acceptable in an immediate dosage composition. This is because the process by which the active agents are slowly released (e.g. formation of shells of liquid crystalline phase as described herein) also serves to retard the passage of solvent from the composition. As a result, the solvent is released over some time (e.g. minutes or hours) rather than instantaneously and so can be better tolerated by the body.

As a general guide, the weight of component c will typically be around 5 to 25% of the total weight of components a), b) and c), or of the total weight of components a), b), c) and d) when component d) is present. This proportion is preferably is in the range 7 to 20%, for example 9 to 18% by weight. For non-parenteral (e.g. per-oral) depots component c) is preferably in the range 5 to 20%. More preferably component c) is in the range 5 to 15% by weight.

In one embodiment applicable to all aspects of the invention, the pre-formulation further comprises component d) at least one polar solvent, which will typically be present at 1 to 20% by weight of components a)+b)+c)+d). Preferably component d) will be greater than 1% by weight of the pre-formulation, for example 1.2-20 wt. %, especially 2-18 wt. %. More preferably component d) is present in the range 5-15 wt. %, especially 6-12 wt. %. Preferably said polar solvent may have a dielectric constant of at least 28 measured at 25° C., more preferably at least 30 measured at 25° C.

Component a)—Diacyl Glycerol/Tocopherol

Component "a" as indicated herein is a neutral lipid component comprising a polar "head" group and also non-polar "tail" groups. Generally the head and tail portions of the lipid will be joined by an ester moiety but this attachment may be by means of an ether, an amide, a carbon-carbon bond or other attachment. Specifically in the pre-formulation of the invention, component a is a diacyl glycerol and has two non-polar "tail" groups.

Mono-acyl ("lyso") lipids are typically less well tolerated in vivo and where present will form a minor part of component a) (e.g. less than 10%). Preferably, for parenteral compositions there will be less than 10% mono-acyl lipids present as a proportion of component a). For non-parenteral (e.g. per-oral) compositions preferably there will be less than 20% mono-acyl lipids present as a proportion of component a). Examples of mono-acyl lipids include glycerol monooleate (GMO).

The two non-polar groups may have the same or a differing number of carbon atoms and may each independently be saturated or unsaturated. Examples of non-polar groups include $C_{16}$-$C_{20}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), and arachidonoyl (C20:4) groups. Thus, typical non-polar chains are based on the fatty acids of natural ester lipids, including palmitic, phytanic, palmitolic, stearic, oleic, elaidic, linoleic, linolenic or arachidonic acids, or the corresponding alcohols. Preferable non-polar chains are $C_{16}$-$C_{20}$ (e.g. $C_{16}$ to $C_{18}$) groups, especially $C_{18}$ groups. It is most preferred if the non-polar tail groups of component a) consists essentially of unsaturated C18 groups. Especially preferred are C18:1 and C18:2 groups (and their mixtures), for example oleyl (C18:1), and/or linoleyl (C18:2) groups. Thus, dioleyl, dilinoleyl and/or oleyl/linoleyl diacyl glycerols and all mixtures thereof are highly suitable.

The diacyl glycerol, when used as all or part of component "a", may be synthetic or may be derived from a purified and/or chemically modified natural sources such as vegetable oils. Mixtures of any number of diacyl glycerols may be used as component a. Most preferably this component will include at least a portion of glycerol dioleate (GDO). A highly preferred example is DAG comprising at least 50%, preferably at least 70% and even comprising substantially 100% GDO. Where the amount of GDO is above 50% or above 70%, much of the remainder (e.g. more than 50% or more than 75% or the remainder) may be dilinoleyl glycerol and/or oleyl linoleyl glycerol.

An alternative or additional highly preferred class of compounds for use as all or part of component a) are tocopherols. As used herein, the term "a tocopherol" is used to indicate the non-ionic lipid tocopherol, often known as vitamin E, and/or any suitable salts and/or analogues thereof. Suitable analogues will be those providing the phase-behaviour, lack of toxicity, and phase change upon exposure to aqueous fluids, which characterise the compositions of the present invention. Such analogues will generally not form liquid crystalline phase structures as a pure compound in water. The most preferred of the tocopherols is tocopherol itself, having the structure below. Evidently, particularly where this is purified from a natural source, there may be a small proportion of non-tocopherol "contaminant" but this will not be sufficient to alter the advantageous phase-behaviour or lack of toxicity. Typically, a tocopherol will contain no more than 10% of non-tocopherol-analogue compounds, preferably no more than 5% and most preferably no more than 2% by weight.

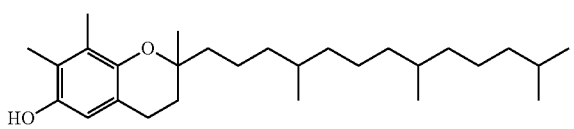

Tocopherol (Vitamin E)

In a further advantageous embodiment of the invention, component a) comprises at least 50%, preferably at least 70% and more preferably consists essentially of tocopherols, in particular tocopherol as shown above.

A preferred combination of constituents for component a) is a mixture of at least one DAG with at least one tocopherol. Preferably the DAG will have C16-C18 alkyl or alkenyl non-polar tail groups, for example oleyl, dioleyl and/or linoleyl groups. Such mixtures include 2:98 to 98:2 by weight tocopherol:GDO, e.g. 10:90 to 90:10 tocopherol:GDO and especially 20:80 to 80:20 of these compounds. Similar mixtures of tocopherol with other DAGs are also suitable.

Component a) may be present in the range 25 to 55% by weight of the total weight of components a), b) and c), or of the total weight of components a), b), c) and d) when component d) is present. Preferably component a) will independently be present in the range 30 to 50 wt. %. Most preferably component a) will be present in the range 35 to 45 wt. %.

Component b)—Phospholipid Component

Component "b" in the present invention is at least one phospholipid component comprising phospholipids having
  i. polar head groups comprising more than 50% phosphatidyl ethanolamine, and
  ii. two acyl chains each independently having 16 to 20 carbons wherein at least one acyl chain has at least one unsaturation in the carbon chain, and there are no more than four unsaturations over the two carbon chains.

As with component a), this component comprises a polar head group and at least one non-polar tail group. The difference between components a) and b) lies principally in the polar group. The non-polar portions may thus suitably be derived from the fatty acids or corresponding alcohols considered above for component a). The phospholipid component b) comprises phospholipids containing two acyl groups which may be the same or different.

Preferred phospholipid polar "head" groups include phosphatidylcholine (PC), phosphatidylethanolamine (PE), sphingomyelin (SM), phosphatidylinositol (PI) and comprise at least 50% PE. The most preferred polar group is thus phosphatidylethanolamine (PE). Phospholipid component b) comprises at least one phospholipid having polar head groups comprising more than 50% PE, preferably at least 75% PE, for example at least 80% PE or at least 90% PE. Preferably phospholipid component b) comprises at least one phospholipid having polar head groups consisting of essentially 100% phosphatidyl ethanolamine (e.g. greater than 90% PE or greater than 95% PE).

In one embodiment applicable to all aspects of the invention component b) further comprises at least one phospholipid having
  i. polar head groups comprising more than 90% phosphatidyl choline, and
  ii. two acyl chains each independently having 16 to 20 carbons wherein at least one acyl chain has at least one unsaturation in the carbon chain, and there are no more than four unsaturations over the two carbon chains.

Preferably phospholipid component b) will comprise phospholipids selected from phosphatidyl ethanolamines, and mixtures of phosphatidyl ethanolamines with at least one phospholipid selected from phosphatidyl cholines, phosphatidyl inositols, and sphingomyelins. It is preferred if phospholipid component b) comprises at least 50% PE, e.g. more than 50% PE, preferably at least 70% PE and most preferably at least 80% PE. Component b) may consist essentially of 100% PE (e.g. >95% PE).

A typical phospholipid component b) may comprise PE and PC in a ratio in the range of 51:49 to 90:10, for example 70:30 to 80:20.

Preferably component b) comprises a maximum of 25% of phosphatidylcholine (PC), for example 20% PC or in the range of 0 to 10% PC. Preferably component b) comprises a maximum of 25% of phosphatidylinositol (PI), for example 0 to 10% PI. Preferably component b) comprises a maximum of 25% of sphingomyelin, for example 0 to 10% sphingomyelin. Most preferably component b) comprises a maximum of 25% of the combined contributions of PC, PI and/or sphingomyelin, for example 0 to 10%.

Most preferably, phospholipid component b) comprises dioleoyl phosphatidyl ethanolamine (DOPE), Soy PE and/or Egg PE, or mixtures of at least one of DOPE/Soy PE/Egg PE with at least one of dioleoyl phosphatidyl choline (DOPC), Soy PC (SPC), and/or Egg PC (EPC).

The phospholipid portion may be derived from a natural source. Suitable sources of phospholipids include egg, heart (e.g. bovine), brain, liver (e.g. bovine), milk and plant sources including soybean. Particularly preferred are Soy and Egg phospholipids, especially Soy PE and/or Egg PE. Such sources may provide one or more constituents of component b, which may comprise any mixture of phospholipids. Preferably component b) comprises Soy PE and/or Egg PE.

Phospholipid component b) (as a whole) preferably forms a reversed hexagonal liquid crystalline phase at 37° C. in the presence of excess aqueous phase, for example excess water.

In a preferred embodiment component b) comprises DOPE and DOPC and/or Soy PC and/or Egg PC, preferably in a ratio in the range of 65:35 to 90:10, such as 85:15, for example 70:30 to 80:20.

Since the pre-formulations of the invention are to be administered to a subject for the controlled release of an active agent, it is preferable that the components a and b are biocompatible. In this regard, it is preferable to use, for example, diacyl glycerol and phospholipids rather than mono-acyl (lyso) compounds. A notable exception to this is tocopherol, as described above. Although having only one alkyl chain, this is not a "lyso" lipid in the convention sense. The nature of tocopherol as a well tolerated essential vitamin makes it highly biocompatible.

It is furthermore most preferable that the lipids and phospholipids of components a and b are naturally occurring (whether they are derived from a natural source or are of synthetic origin). Naturally occurring lipids tend to be tolerable both systemically and locally with lesser amounts of inflammation and reaction from the body of the subject. Not only is this more comfortable for the subject but it may increase the residence time of the resulting depot composition, especially for parenteral depots, since less immune system activity is recruited to the administration site. In certain cases it may, however, be desirable to include a portion of a non-naturally-occurring lipid in components a and/or b. This might be, for example an "ether lipid" in which the head and tail groups are joined by an ether bond rather than an ester. Such non-naturally-occurring lipids may be used, for example, to alter the rate of degradation of the resulting depot-composition by having a greater or lesser solubility or vulnerability to breakdown mechanisms present at the site of active agent release. Although all proportions fall within the scope of the present invention, generally, at least 50% of each of components a and b will be naturally occurring lipids. This will preferably be at least 75% and may be up to substantially 100%. Particularly preferred are Soy and/or Egg derived lipids.

Two particularly preferred combinations of components a and b are GDO with DOPE, and tocopherol with DOPE, especially in the region 35-45 wt. % component a), 35-45 wt. % component b), and 5-20 wt. % component c), of the total weight of components a), b) and c) (and d) where present). In one embodiment, the solvent component c) does not comprise PG or other polar solvents present in optional component d). This applies particularly when optional polar solvent component d) is present.

In addition to amphiphilic components a and b, the pre-formulations of the invention may also contain additional amphiphilic components at relatively low levels. In one embodiment of the invention, the pre-formulation contains up to 10%, preferably up to 7% (by weight of components a) and b)) of a charged amphiphile, particularly an anionic amphiphile such as a fatty acid. Preferred fatty acids for this purpose include caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable fatty acids are palmitic, stearic, oleic and linoleic acids, particularly oleic acid.

Component b) may be present in the range 25 to 55% by weight of the total weight of components a), b) and c). Preferably component b) will be present in the range 30 to 50 wt. %. Most preferably component b) will present in the range 35 to 45 wt. % of the total weight of components a), b) and c), or of the total weight of components a), b), c) and d) when component d) is present.

Components a) and b) may independently be present in the range 25 to 55% by weight of the total weight of components a), b) and c), or of the total weight of components a), b), c) and d) when component d) is present. Preferably components a) and b) will independently be present in the range 30 to 50 wt. %. Most preferably components a) and b) will independently be present in the range 35 to 45 wt. %.

Preferably the total of components a) and b) will be at least 60% by weight of components a), b) and c), or of the total weight of components a), b), c) and d) when component d) is present.

The total of the lipid components, i.e. component a) and component b), will preferably be at least 50% by weight of the complete pre-formulation. In one embodiment, the total of components a), b), c), optional component d) where present, and any optional active agent where present will amount to at least 70 wt. % of the total composition. This may preferably be at least 80, more preferably at least 90 wt. % and in one embodiment the pre-formulation will consist essentially of these components. By "consists essentially of" as used herein is indicated an amount of at least 90%, preferably at least 95% by weight.

Component c)—Solvent

Component "c" of the pre-formulations of the invention is an oxygen containing organic solvent. Since the pre-formulation is to generate a depot composition following administration (e.g. in vivo), upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

The solvent is such that a relatively small addition to the composition comprising a and b, i.e. below 20% (by wt), or more preferably below 10%, give a large viscosity reductions of one order of magnitude or more. As described herein, the addition of 10% solvent can give a reduction of two, three or even four orders of magnitude in viscosity over the solvent-free composition, even if that composition is a solution or $L_2$ phase containing no solvent, or an unsuitable solvent such as water (subject to the special case considered below), or glycerol.

Typical solvents suitable for use as component c include at least one solvent selected from alcohols, ketones, esters (including lactones), ethers, amides and sulphoxides. Examples of suitable alcohols include ethanol and isopropanol. Monools are preferred to diols and polyols. Where diols or polyols are used, this is preferably in combination with an at least equal amount of monool or other preferred solvent. Examples of ketones include acetone and propylene carbonate. Suitable ethers include diethylether, glycofurol, diethylene glycol monoethyl ether, dimethylisobarbide, and polyethylene glycols. Suitable esters include ethyl acetate and isopropyl acetate and dimethyl sulphide is as suitable sulphide solvent. Suitable amides and sulphoxides include N-methyl pyrrolidone (NMP), 2-pyrrolidone, dimethylacetamide (DMA) and dimethylsulphoxide (DMSO), respectively. Less preferred solvents include dimethyl isosorbide, tetrahydrofurfuryl alcohol, diglyme and ethyl lactate.

Since the pre-formulations are to be administered to a living subject, it is necessary that the solvent component c is sufficiently biocompatible. The degree of this biocompatibility will depend upon the application method and since component c may be any mixture of solvents, a certain amount of a solvent that would not be acceptable in large quantities may evidently be present. Overall, however, the solvent or mixture forming component c must not provoke unacceptable reactions from the subject upon administration. Generally such solvents will be hydrocarbons or preferably oxygen containing hydrocarbons, both optionally with other substituents such as nitrogen containing groups. It is preferable that little or none of component c contains halogen substituted hydrocarbons since these tend to have lower biocompatibility. Where a portion of halogenated solvent such as dichloromethane or chloroform is necessary, this proportion will generally be minimised. Where the depot composition is to be formed non-parenterally a greater range of solvents may evidently be used than where the depot is to be parenteral.

Component c as used herein may be a single solvent or a mixture of suitable solvents but will generally be of low viscosity. This is important because one of the key aspects of the present invention is that it provides pre-formulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C.

The solvent component c will generally be at least partially lost upon in vivo formation of the depot composition, or diluted by absorption of water from the surrounding air and/or tissue. It is preferable, therefore, that component c be at least to some extent water miscible and/or dispersible and at least should not repel water to the extent that water absorption is prevented. In this respect also, oxygen containing solvents with relatively small numbers of carbon atoms (for example up to 10 carbons, preferably up to 8 carbons) are preferred. Obviously, where more oxygens are present a solvent will tend to remain soluble in water with a larger number of carbon atoms. The carbon to heteroatom (e.g. N, O, preferably oxygen) ratio will thus often be around 1:1 to 6:1, preferably 2:1 to 4:1. Where a solvent with a ratio outside one of these preferred ranges is used then this will preferably be no more than 75%, preferably no more than 50%, in combination with a preferred solvent (such as ethanol). This may be used, for example to decrease the rate of evaporation of the solvent from the pre-formulation in order to control the rate of liquid crystalline depot formation.

Preferably, component c) is selected from alcohols, ketones, esters, ethers, amides, sulphoxides and mixtures thereof. More preferably component c) is selected from monool alcohols, diols, triols, ethers, ketones and amides. Most preferred solvents for component c) are selected from the group consisting of low molecular weight PEGs (200-500 Dalton), ethanol, NMP, or mixtures thereof. Especially preferred are ethanol and NMP or mixtures thereof.

As mentioned above, as a general guide, the weight of component c will typically be around 5 to 25% of the total weight of components a), b) and c), or of the total weight of components a), b), c) and d) when component d) is present. This proportion is preferably (especially for injectable depots) in the range 7 to 20%, for example 9 to 18% by weight.

Optional Component d)—Polar Solvent

Although it has previously been suggested that lipid controlled-release compositions should be formulated substantially in the absence of water, in order to avoid the conversion to high-viscosity liquid crystalline phases, it has now been established that a small and carefully controlled amount of a polar solvent such as water can provide considerable benefits. In particular, the inclusion of this polar solvent (preferably comprising water) allows further improvements in controlling the initial release of active agent, allows higher stable loading of some peptide active agents, provides faster depot formation and/or provides further reduced discomfort upon injection. Any one of these factors potentially provides a significant improvement in the context of therapeutic drug delivery, patient health and/or patient compliance.

The pre-formulations of the present invention can thus also contain a polar solvent, component d), in addition to component c). A suitable amount of the combined solvents, i.e. c)+d), will typically be greater than 1% by weight of the pre-formulation, for example 5-20 wt. %. More preferably component d) is present in the range 5-15%, especially 6-12%, by weight of the total composition. Component d) is preferably water, propylene glycol or mixtures thereof. In one preferred aspect, the pre-formulations of the invention contain ethanol as component c) with water and/or propylene glycol as component d).

In one embodiment the pre-formulation comprises at least 1.5% (e.g. at least 4.5%) water as part of component d) (by weight of the total composition) with the remainder being propylene glycol. At least 5% water with the balance of component d) being PG is preferred. Component d) may comprise or consist of water.

In an alternative embodiment, component d) may comprise or consist of propylene glycol.

Polar solvents suitable as optional component d) typically may have a dielectric constant of at least 28 when measured at 25° C., for example at least 30 when measured at 25° C.

Preferred polar solvents include water, propylene glycol (PG) and N-Methyl-2-pyrrolidone, as well as binary and ternary mixtures thereof.

Preferably, polar solvents suitable as optional component d) are not included as part of the main solvent component c). For example, component c) may exclude water, propylene glycol and/or mixtures thereof.

Preferably the total level of components c) and d) is not more than 35 wt. %, preferably not more than 30 wt. %, preferably 10-30 wt. %, most preferably 12-25% by weight of components a)+b)+c)+d).

The ratio of components c) and d) will also have potential advantages in the compositions of the invention. In particular, by inclusion of some polar solvent which is miscible with the mono-alcohol component (especially water), the slight sensation that may be caused at the injection site from the alcohol content can be substantially eliminated. Thus, in one embodiment, the weight ratio of components c):d) may be in the range 30:70 to 70:30, more preferably 40:60 to 60:40. In one embodiment, the amount of alcohol component c) by weight is no greater than the amount of polar solvent d). Ratios of c):d) ranging from 30:70 to 50:50 are thus appropriate in such an embodiment. Approximately equal amounts of components c) and d) are highly appropriate.

In a preferred combination, component a) is GDO or tocopherol, component b) is DOPE or a mixture of DOPE and PC, component c) is ethanol, NMP or mixtures thereof, and component d) is water, PG or mixtures thereof, in the ranges 35-45 wt. % component a), 35-45 wt. % component b), 2-20 wt. % component c), and 5-15 wt. % component d).

A highly preferred combination for the pre-formulation is GDO, DOPE, ethanol, and water/propylene glycol or mixtures thereof. As indicated above, appropriate amounts of each component suitable for the combination are those amounts indicated herein for the individual components, in any combination.

Preferably, components a), b) and c) make up 80 to 95% by weight of the total composition and component d) makes up 10 to 20% by weight of the total composition.

Peptide Active Agent

The pre-formulations of the present invention contain one or more peptide active agent comprising at least one somatostatin receptor agonist (described equivalently as "active agents" herein). Active agents will be formulated at a level sufficient to provide an in vivo concentration at a functional level (including local concentrations for topical compositions). Under some circumstances one or more of components a, b and/or c may also be an active agent, although it is preferred that the active agent should not be one of these components. Most preferred active agents are constrained peptides of 6-30 α-amino acids (e.g. 6-10), preferably comprising or consisting of at least one selected from the group consisting of SST-14, SST-28, octreotide, lanreotide, pasireotide and vapreotide or salts thereof.

Particularly suitable active agents include those which would normally have a short residence time in the body due to rapid breakdown or excretion and those with poor oral bioavailability. These include peptide based active agents in their native or modified forms. By administering such agents in the form of a depot composition formed from the pre-formulation of the present invention, the agents are provided at a sustained level for a length of time which may stretch to days, weeks or even several months in spite of having rapid clearance rates. This offers obvious advantages in terms of stability and patient compliance over dosing multiple times each day for the same period. In one preferred embodiment, the active agent thus has a biological half life (upon entry into the blood stream) of less than 1 day, preferably less than 12 hours and more preferably less than 6 hours. In some cases this may be as low as 1-3 hours or less. Suitable agents are also those with poor oral bioavailability relative to that achieved by injection, for where the active agent also or alternatively has a bioavailability of below 20%%, or preferably below 2%, especially below 0.2%, and most preferably below 0.1% in oral formulations.

Peptide based active agents include human and veterinary drugs selected from the group consisting of somatostatins and their related peptides. An interesting class of peptide active agents suitable for the invention are peptide hormones, including those of the class of pancreatic hormones including somatostatin. All synthetic peptides designed to have similar receptor affinity spectrums as the above mentioned peptides are also very suitable for the invention.

A further considerable advantage of the depot compositions of the present invention is that active agents are released gradually over long periods without the need for repeated dosing. The compositions are thus highly suitable for situations where patient compliance is difficult, unreliable or where a level dosage is highly important, such as mood-altering actives, those actives with a narrow therapeutic window, and those administered to children or to people whose lifestyle is incompatible with a reliable dosing regime and for "lifestyle" actives where the inconvenience of repeated dosing might outweigh the benefit of the active. Cationic peptides are particularly suitable for use where a portion of the pre-formulation comprises an anionic amphiphile such as a fatty acid or anionic lipid, including phosphatidic acid, phosphatidylglycerol, phosphatidylserine. In this embodiment, preferred peptides include pasireotide, octreotide and lanreotide.

In one preferred aspect of the present invention, the composition of the invention is such that a reversed micellar cubic ($I_2$) phase, or a mixed phase including $I_2$ phase is formed upon exposure to aqueous fluids and a polar active agent is included in the composition. Particularly suitable polar active agents include peptide including those listed above. Of particular interest in this aspect are the peptide octreotide and other somatostatin related peptides.

A particular advantage of the present invention when used in combination with protein/peptide active agents is that aggregation of the active agent is suppressed. In one preferred embodiment, the present invention thus provides a depot precursor and particularly a depot composition as described herein comprising at least one peptide active agent wherein no more than 5% of the active agent is in aggregated form. Preferably no more than 3% is aggregated and most preferably no more than 2% (especially less than 2%) is in aggregated form. This stabilisation of non-aggregated protein is highly advantageous from the point of view of high effectiveness, low side effects and predictable absorption profile. Furthermore, it is increasingly expected that peptide therapeutics will have low levels of protein aggregation in order to secure regulatory approval.

Somatostatins (Growth Hormone Release Inhibiting Factors, SSTs) are natural peptide hormones with a wide distribution in animals, acting as neurotransmitters in the central nervous system, and having diverse paracrine/autocrine regulatory effects on several tissues. Two biologically active products are known in higher species, SST-14 and SST-28, a congener of SST-14 extended at the N-terminus.

SST-14 is a 14 residue cyclic peptide hormone having the sequence Ala-Gly-Cys-Lys-Asn-Phe-Phe-Trp-Lys-Thr-Phe-Thr-Ser-Cys, where the two cysteine residues are connected by a disulphide bridge to generate a type II β-turn at the key binding sequence of Phe-Trp-Lys-Thr. The biological half-life of natural SST-14 is very short (1-3 minutes) and so it is not, in itself, a viable therapeutic in current formulations, but an increasing number of somatostatin receptor agonists are becoming available with higher activities and/or longer clearance times in vivo.

Somatostatin receptor agonists (SRAs), such as SST-14, SST-28, octreotide, lanreotide, vapreotide, pasireotide (SOM 230) and related peptides, are used or indicated in the treatment of a variety of conditions where they are typically administered over an extended period. SRAs form a preferred group of active agents for use in the present invention.

Octreotide, for example, is the synthetic octapeptide with sequence D-Phe-Cys-Phe-D-Trp-Lys-Thr-Cys-Thr-ol (2-7 disulphide bridge) and is typically administered as an acetate salt. This SST-14 derivative retains the key Phe-(D)Trp-Lys-Thr β-turn required for in vivo SST-like activity but, in contrast to the natural hormone, has a terminal half-life of around 1.7 hours. Octreotide is used in treatment of conditions including carcinoid tumours and acromegaly, and is typically administered over a sustained period of weeks, or more commonly many months or years. Somatostatin receptor agonists are of particular interest for the treatment of many different types of cancers since a wide variety of tumours are found to express somatostatin receptors (SSTRs). There are five known types of SSTRs (SSTR1-SSTR5), showing equally high affinity for SST-14. The most investigated somatostatin receptor agonists, including octreotide, show high selectivity for SSTR2 and SSTR5; thus, octreotide is of particular interest for the treatment of tumours expressing these types of receptors.

The most common "simple" formulation of Octreotide is "Sandostatin"® from Novartis. This is an aqueous solution for subcutaneous (s.c) injection, and a 100 µg dose reaches a peak concentration of 5.2 ng/ml at 0.4 hours post injection. The duration of action can be up to 12 hours but s.c. dosing is generally carried out every 8 hours. Evidently, s.c. injection 3 times daily for periods of months or years is not an ideal dosing regime.

Pasireotide is a multireceptor-targeted somatostatin analogue with high affinity for somatostatin receptor subtypes sstr1,2,3 and sstr5 that has been developed for the treatment of neuroendocrine diseases. Two formulations of pasireotide have currently been developed: an immediate-release formulation for subcutaneous (sc) injection and a long-acting-release (LAR) formulation. The structure of pasireotide is as follows:

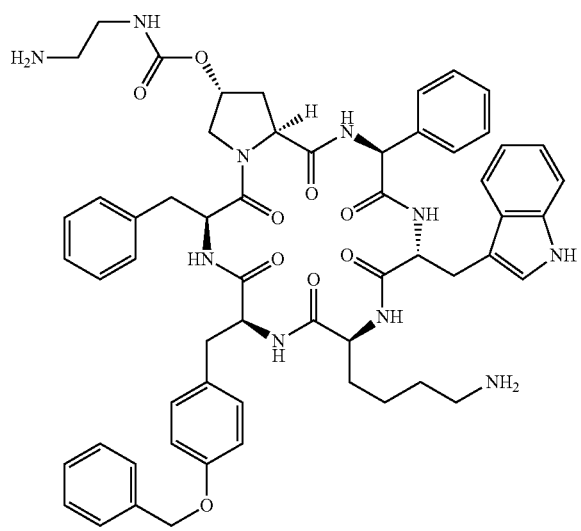 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O]

Pasireotide was initially developed by Novartis Pharma as a treatment for Cushing's disease/syndrome and acromegaly, but has potential applicability in the treatment of several conditions for which somatostatin analogues such as octreotide are indicated, including carcinoid tumours.

Following a single subcutaneous dose of pasireotide, human plasma levels typically peak quickly, at around 15 minutes to 1 hour after dosing, with an initial half-life of 2-3 hours following that peak. Although clearance half-life is greater for later phases of the decline, it is clear that the Cmax/Cave for such a delivery will be rather high.

Pasireotide LAR is a long acting formulation of pasireotide which addresses some of the above issues. However, this is a polymer microparticle based system with the inherent limitations of such a system, as are known in the art and described herein above.

Carcinoid tumours are intestinal tumour arising from specialised cells with paracrine functions (APUD cells). The primary tumour is commonly in the appendix, where it is clinically benign. Secondary, metastatic, intestinal carcinoid tumours secrete excessive amounts of vasoactive substances, including serotonin, bradykinin, histamine, prostaglandins, and polypeptide hormones. The clinical result is carcinoid syndrome (a syndrome of episodic cutaneous flushing, cyanosis, abdominal cramps, and diarrhea in a patient with valvular heart disease and, less commonly, asthma and arthropathy). These tumours may grow anywhere in the gastrointestinal tract (and in the lungs) with approximately 90% in the appendix. The remainder occurs in the ileum, stomach, colon or rectum. Currently, treatment of carcinoid syndrome starts with i.v. bolus injection followed by i.v. infusion. When sufficient effect on symptoms has been established, treatment with a depot formulation of octreotide formulated in ploy lactic-co-glycolic acid (PLGA) microspheres is started. However, during the first two weeks or more after injection of the depot, daily s.c. injections with octreotide are recommended to compensate for the slow release from the PLGA spheres.

The pre-formulations of the present invention contain at least one peptide active agent comprising at least one somatostatin receptor agonist (which are intended by any reference to "active agents" herein). Since SST-14 is a peptide hormone, typical somatostatin receptor agonists will be peptides, especially of 14 or fewer amino acids. Preferably such peptides will be structurally constrained such as by being cyclic and/or having at least one intra-molecular cross-link. Amide, ester or particularly disulphide crosslinks are highly suitable. Preferred constrained peptides will exhibit a type-2 β turn. Such a turn is present in the key region of somatostatin. Peptides may contain only amino acids selected from those 20 α-amino acids indicated in the genetic code, or more preferably may contain their isomers and other natural and non-natural amino acids, (generally α, β or γ, L- or D-amino acids) and their analogues and derivatives. The term "somatostatin receptor agonist" as used herein may optionally also encompass SST-14 and/or SST-28, since these are viable peptide actives when formulated as salts in the very high performance slow-release formulations described herein.

Amino acid derivatives and amino acids not normally used for protein synthesis are especially useful at the termini of the peptides, where the terminal amino or carboxylate group may be substituted by or with any other functional group such as hydroxy, alkoxy, ester, amide, thio, amino, alkyl amino, di- or tri-alkyl amino, alkyl (by which is meant, herein throughout $C_1$-$C_{18}$ alkyl, preferably $C_1$-$C_8$ alkyl e.g. methyl, ethyl, n-propyl, isopropyl, n-butyl, iso-, sec- or t-butyl etc.), aryl (e.g phenyl, benzyl, napthyl etc) or other functional groups, preferably with at least one heteroatom and preferably having no more than 10 atoms in total, more preferably no more than 6.

Particularly preferred somatostatin receptor agonists are constrained peptides of 6 to 10 α-amino acids, of which particular examples include octreotide, lanreotide (of sequence $NH_2$-(D)Naph-Cys-Tyr-(D)Trp-Lys-Val-Cys-Thr-$CONH_2$ and its cyclic derivative of sequence $NH_2$-(D)Naph-Cys-Tyr-(D)Phe-Lys-Val-Cys-Thr-$CONH_2$ both having a Cys-Cys intramolecular disulphide crosslink), SOM 230 (see structure above) and vapreotide. Most preferred are octreotide and pasireotide.

The somatostatin receptor agonist will be formulated as 0.1 to 10% by weight of the total formulation. Typical values will be 0.5 to 9%, preferably 1 to 8% and more preferably 1 to 7%. A somatostatin receptor agonist content of 2-5% is most preferable.

Doses of the somatostatin receptor agonist suitable for inclusion in the formulation, and thus the volume of formulation used, will depend upon the release rate (as controlled, for example by the solvent type and amount use) and release duration, as well as the desired therapeutic level, the activity and the rate of clearance of the particular active chosen. Typically an amount of 1 to 500 mg per dose would be suitable for providing a therapeutic level for between 7 and 90 days. This will preferably be 5 to 300 mg. For octreotide, the level will typically be around 10 to 180 mg (e.g. for a 30 to 90 day duration). Preferably, the amount of octreotide will be around 0.2 to 3 mg per day between injections. Thus a depot administered every 30 days would have 6 to 90 mg or a 90 day depot have 18 to 270 mg of octreotide.

For Pasireotide, the dosage would typically be an amount of around 0.05 to 40 mg per week of depot duration, preferably 0.1 to 20 mg per week duration (e.g. 1 to 5 mg per week) for a duration of 1 to 24 weeks, preferably 2 to 16 (e.g. 3, 4, 8, 10 or 12) weeks. In an alternative embodiment the pre-formulation may be formulated for dosing weekly (e.g. every 7±1 days). A total dose of 0.05 to 250 mg of Pasireotide per dose would be suitable for providing a therapeutic level for between 7 and 168 days. This will preferably be 0.1 to 200 mg, e.g. 0.2 to 150 mg, 0.1 to 100 mg, 20 to 160 mg etc. Evidently, the stability of the active and effects on the release rate will mean that the loading to duration may not be a linear relationship. A depot administered every 30 days might have, for example 0.2 to 20 mg of Pasireotide, or a 90 day depot might have 30 to 60 mg of Pasireotide.

Where the salt of a peptide active agent, such as an SRA, is used in the formulations of the present invention, this will be a biologically tolerable salt. Suitable salts include the tartrate, acetate, pamoate, chloride or bromide salts. The pamoate and chloride salts are preferred. The pamoate salt is most preferred.

The amount of peptide active agent to be formulated with the pre-formulations of the present invention will depend upon the functional dose and the period during which the depot composition formed upon administration is to provide sustained release. Typically, the dose formulated for a particular agent will be around the equivalent of the normal daily dose multiplied by the number of days the formulation is to provide release. Evidently this amount will need to be tailored to take into account any adverse effects of a large dose at the beginning of treatment and so this will generally be the maximum dose used. The precise amount suitable in any case will readily be determined by suitable experimentation.

The pre-formulation of the invention will comprise 0.1-10 wt. % of said active agent by weight of components a)+b)+c)(+d) where present).

Preferably the active agent is selected from somatostatins SST-14 and SST-28 and somatostatin receptor (SSTR) agonists, e.g. octreotide, lanreotide, vapreotide, pasireotide Preferably the active agent is selected from octreotide, pasireotide and mixtures thereof. Most preferably the active agent comprises pasireotide pamoate and octreotide chloride.

Administration

As mentioned above, the pre-formulation of the invention may be administered and the methods of the invention applied using a route appropriate for the condition to be treated and the peptide active agent used. The term "parenteral" as used herein is given its established meaning of "through the skin" rather than all "non-oral" routes.

Thus parenteral primarily indicates administration by injection, infusion and similar techniques (such as needleless injection). The term "non-parenteral" thus covers application routes other than through the skin. A parenteral depot will thus be formed by parenteral (e.g. injectable, such as by subcutaneous or intramuscular injection) administration while a non-parenteral (e.g. per-oral, topical) depot composition may be formed by administration to the surface of skin, mucous membranes and/or nails, to ophthalmological, nasal, oral or internal surfaces or to cavities such as nasal, rectal, vaginal or buccal cavities, the periodontal pocket or cavities formed following extraction of a natural or implanted structure or prior to insertion of an implant (e.g a joint, stent, cosmetic implant, tooth, tooth filling or other implant).

In a preferred embodiment, the pre-formulations of the present invention will generally be administered parenterally. This administration will generally not be an intravascular method but will preferably be subcutaneous intracavitary or intramuscular. Typically the administration will be by injection, which term is used herein to indicate any method in which the formulation is passed through the skin, such as by needle, catheter or needle-less injector. In parenteral (especially subcutaneous (s.c.)) depot precursors, preferred active agents are those suitable for systemic administration of somatostatin receptor agonists, also referred to as somatostatin analogues, including octreotide, pasireotide and lanreotide.)

Phase Structures

The pre-formulations of the present invention provide non-lamellar liquid crystalline depot compositions upon exposure to aqueous fluids, especially in vivo and in contact with body surfaces. In a preferred embodiment the liquid crystalline phases of the invention are formed in situ.

As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase, preferably reversed. By use of the pre-formulations of the present invention it is possible to generate any phase structure present in the phase-diagram of components a and b with water. This is because the pre-formulations can be generated with a wider range of relative component concentrations than previous lipid depot systems without risking phase separation or resulting in highly viscous solutions for injection. In particular, the present invention provides for the use of phospholipid concentrations above 50% relative to the total amphiphile content. This allows access to phases only seen at high phospholipid concentrations, particularly the hexagonal liquid crystalline phases.

Preferably in the pre-formulation of the invention the liquid crystalline phase structure formed upon contact with an aqueous fluid is a reversed hexagonal phase structure ($H_2$) and/or a reversed cubic phase structure ($I_2$) or a mixture or intermediates thereof. With intermediates we refer to phases with mean curvatures between the mean curvature of $H_2$ and $I_2$ phases, respectively, and which position in a phase diagram is between these two phases in case both are present. Preferably the liquid crystalline phase structure is selected from $H_2$, $I_2$ or mixtures thereof.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which an $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

In a highly advantageous embodiment, the compositions of the invention may form an $I_2$ phase, or a mixed phase including $I_2$ phase upon contact with water. The $I_2$ phase is a reversed cubic liquid crystalline phase having discontinuous aqueous regions. This phase is of particular advantage in the controlled release of active agents and especially in combination with polar active agents, such as water soluble actives because the discontinuous polar domains prevent rapid diffusion of the actives. Depot precursors in the $L_2$ are highly effective in combination with an $I_2$ phase depot formation. This is because the $L_2$ phase is a so-called "reversed micellar" phase having a continuous hydrophobic region surrounding discrete polar cores. $L_2$ thus has similar advantages with hydrophilic actives.

In transient stages after contact with body fluid the composition can comprise multiple phases since the formation of an initial surface phase will retard the passage of solvent into the core of the depot, especially with substantial sized administrations of internal depots. Without being bound by theory, it is believed that this transient formation of a surface phase, especially a liquid crystalline surface phase, serves to dramatically reduce the "burst/lag" profile of the present compositions by immediately restricting the rate of exchange between the composition and the surroundings. Transient phases may include (generally in order from the outside towards the centre of the depot): $H_2$ or $L_\alpha$, $I_2$, $L_2$, and liquid (solution). It is highly preferred that the composition of the invention is capable forming at least two and more preferably at least three of these phases simultaneously at transient stages after contact with water at physiological temperatures. In particular, it is highly preferred that one of the phases formed, at least transiently, is the $I_2$ phase.

It is important to appreciate that the pre-formulations of the present invention are of low viscosity. As a result, these pre-formulations must not be in any bulk liquid crystalline phase since all liquid crystalline phases have a viscosity significantly higher than could be administered by syringe or spray dispenser. The pre-formulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than or about 10 wt % of solvent (component c) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the oxygen-containing, low viscosity solvents specified herein.

Upon administration, the pre-formulations of the present invention undergo a phase structure transition from a low viscosity mixture to a high viscosity (generally tissue adherent) depot composition. Generally this will be a transition from a molecular mixture, swollen $L_2$ and/or L3 phase to one or more (high viscosity) liquid crystalline phases such as normal or reversed hexagonal or cubic liquid crystalline phases or mixtures thereof. As indicated above, further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. up to 30 minutes, preferably up to 10 minutes, more preferably 5 minutes of less). The remainder of the composition may change phase to a liquid crystalline phase more slowly by diffusion and/or as the surface region disperses.

In one preferred embodiment, the present invention thus provides a pre-formulation as described herein of which at least a portion forms a hexagonal liquid crystalline phase upon contact with an aqueous fluid. The thus-formed hexagonal phase may gradually disperse, releasing the active agent, or may subsequently convert to a cubic liquid crystalline phase, which in turn then gradually disperses. It is believed that the hexagonal phase will provide a more rapid release of active agent, in particular of hydrophilic active agent, than the cubic phase structure, especially the $I_2$ and L2 phase. Thus, where the hexagonal phase forms prior to the cubic phase, this will result in an initial release of active agent to bring the concentration up to an effective level rapidly, followed by the gradual release of a "maintenance dose" as the cubic phase degrades. In this way, the release profile may be controlled.

Without being bound by theory, it is believed that upon exposure (e.g. to body fluids), the pre-formulations of the invention lose some or all of the organic solvent included therein (e.g. by diffusion and/or evaporation) and take in aqueous fluid from the bodily environment (e.g. moist air close to the body or the in vivo environment) such that at least a part of the formulation generates a non-lamellar, particularly liquid crystalline phase structure. In most cases these non-lamellar structures are highly viscous and are not easily dissolved or dispersed into the in vivo environment and are bioadhesive and thus not easily rinsed or washed away. Furthermore, because the non-lamellar structure has large polar, apolar and boundary regions, it is highly effective in solubilising and stabilising many types of active agents and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

Robustness

The pre-formulations of the invention have improved robustness in comparison with liquid depot formulations known in the art. This is demonstrated by their improved performance in terms of erosion/fragmentation and mechanical/degradation robustness.

A way to study the robustness in vitro is to simulate in vivo conditions by subjecting the lipid gels to a surfactant-rich aqueous environment and subsequently measuring the increased turbidity (or apparent absorbance) of the aqueous phase resulting from surfactant-eroded lipid fragments. Such lipid fragments are released into the solution as suspended particles and give rise to substantial increase in solution turbidity due to light scattering. Bile salts are often used as the surfactant of choice for studying formulation dissolution given their biological relevance and endogenous nature. They are also among the most challenging constituents of the in-vivo environment for a depot system to tolerate and so a system which is resistant to bile salts is potentially of considerable value in drug delivery.

The turbidity factor of the pre-formulations of the invention was measured using the process described in example 3. The turbidity factor may be considered a measure of the robustness of the pre-formulation in respect of erosion/fragmentation, i.e. chemical degradation. The turbidity factor (TF) is thus defined herein as the absorbance (or turbidity) at 600 nm of the aqueous phase resulting from placing a 200 mg aliquot of pre-formulation in 5 ml of a 0.1 wt. % solution of sodium taurocholate in phosphate buffered saline (pH 7.4), at 37° C. for 6 hours under 150 rpm rotation.

The pre-formulations of the invention have a reduced turbidity factor in comparison with that of existing formulations. Preferably the turbidity factor is decreased by at least 50% in comparison with existing pre-formulations. More preferably the turbidity factor of the pre-formulations of the invention is decreased by at least 60% in comparison with existing pre-formulations. For example the turbidity factor of the invention may be equal to or less than half, preferably less than 40% of the turbidity factor of the existing pre-formulation.

It is a considerable and surprising benefit of the present precursor formulations that they show markedly superior resistance to degradation in comparison with corresponding formulations in which the phospholipid component (component b)) is phosphatidyl choline. Thus, for example, the turbidity factor over an equivalent composition in which component b) is PC is decreased by at least 50%. More preferably the turbidity factor of the pre-formulations of the invention are decreased by at least 60% in comparison with equivalent pre-formulations in which component b) is PC (e.g. soy PC). For example the turbidity factor of the invention may be equal to or less than half, preferably less than 40% of the turbidity factor of the corresponding PC-containing pre-formulation.

Preferably the turbidity factor of the pre-formulations according to the invention may be approximately 0.6 or less, for example, 0.4. More preferably the turbidity factor may be 0.3 or less, for example 0.25 or less. Most preferably the turbidity factor may be 0.2 or less.

In comparison with existing liquid depot pre-formulations (such as those in which component b) is PC, such as soy PC), preferably the turbidity factor of the pre-formulations of the invention is reduced by at least a factor of three, for example a factor of five, more preferably a factor or eight and most preferably a factor of ten.

In a preferred embodiment, the absorbance value of a PE-based pre-formulation measured according to example 3 will be in the range of one third to one eighth of the corresponding PC-based formulation. For example, a GDO/PE based pre-formulation may have an absorbance value of one third to one eighth of the corresponding GDO/PC composition.

It is a particular and unexpected advantage of the present pre-formulations that they show remarkable resistance to bile acid degradation. This has considerable advantages in providing compositions that may be administered orally and will persist through the digestive tract for some time without being broken down/digested. In particular, the precursor formulations of the present invention are useful for the delivery of active agents to the GI tract. Since the composition furthermore protects the entrained active agent from the conditions of the GI tract, this embodiment may be applied in combination with actives that are susceptible to breakdown in the GI tract, such as peptides. Many peptides are described herein and they may be used appropriately in this embodiment. Delivery of an active agent to a portion of the GI tract below the bile duct is a highly preferred embodiment that may be applied to all appropriate aspects of the invention. The pre-formulations may thus be for delivery of an active agent to the GI tract below the bile duct, etc. Methods of treatment and similar applications may correspondingly be for treatment of a condition in a region of the GI tract below the bile duct.

In combination with the features and preferred features indicated herein, the pre-formulations of the invention may have one or more of the following preferred features independently or in combination:

The pre-formulation forms a liquid crystalline phase structure which is bioadhesive;

Preferably said liquid crystalline phase structure is a reversed hexagonal phase structure or a reversed cubic phase structure or mixtures thereof, such as $H_2$ and/or $I_2$ or mixtures thereof;

The non-polar tail groups of component a) each independently consist essentially of unsaturated C18 groups; or component a) consists essentially of at least one tocopherol; or component a) consists essentially of a mixture of glycerol dioleate (GDO) and tocopherol;

Component b) is selected from phosphatidyl ethanolamines, or mixtures of phosphatidyl ethanolamines with at least one selected from phosphatidyl cholines, phosphatidyl inositols and sphingomyelins;

The phospholipid component b) comprises at least 50% PE, preferably at least 75% PE and most preferably essentially 100% PE;

The phospholipid component b) comprises 10-49% PC, for example 20% PC;

The phospholipid component b) comprises a phospholipid having polar head groups consisting of essentially 100% phosphatidyl ethanolamine;

The phospholipid component b) further comprises a phospholipid having polar head groups consisting of greater than 90% phosphatidyl choline;

The pre-formulation has a viscosity in the range of 0.1 to 5000 mPas;

The pre-formulation has a molecular solution, $L_2$ and/or $L_3$ phase structure;

The pre-formulation has a ratio of a) to b) of between 80:20 and 5:95 by weight;

Component c) is selected from alcohols, ketones, esters, ethers, amides, sulphoxides and mixtures thereof;

The pre-formulation further comprises component d) 1 to 20 wt. % of at least one polar solvent by weight of components a)+b)+c)+d);

The polar solvent has a dieletric constant of at least 28 measured at 25° C., preferably at least 30 measured at 25° C.;

Component d) is selected from water, propylene glycol and mixtures thereof;

Component d) comprises at least 2% water;

The pre-formulation additionally comprises up to 10% by weight of a)+b) of a charged amphiphile;

The pre-formulation has 0.1-10 wt. % of said active agent by weight of components a)+b)+c)+d);

The active agent is selected from Said drug is selected from SOM14, SOM28, octreotide, lanreotide, vapreotide, pasireotide, and mixtures thereof;

The pre-formulation is administrable by injection;

The pre-formulation is administrable by spraying, dipping, rinsing, application from a pad or ball roller, painting, dropping, aerosol spraying or pump spraying;

The pre-formulation has a turbidity factor of below 1, where the turbidity factor (TF) is defined as the absorbance (or turbidity) at 600 nm of the aqueous phase resulting from placing a 200 mg aliquot of pre-formulation in 5 ml of a 0.1 wt. % solution of sodium taurocholate in phosphate buffered saline (pH 7.4), at 37° C. for 6 hours under 150 rpm rotation.

The pre-formulation is injectable and forms a depot providing continuous release of active agent for at least two weeks, preferably at least one month, wherein said active agent comprises at least one selected from:
  a. octreotide;
  b. pasireotide.

In combination with the features and preferred features indicated herein, the method(s) of delivery of the present invention may have one or more of the following preferred features independently or in combination:

The method comprises the administration of at least one formulation with one or more preferred features as indicated above;

The method comprises the administration of at least one pre-formulation as described herein by subcutaneous injection, intramuscular injection, intra-cavity injection through tissue, intra-cavity injection into an open cavity without tissue penetration, spraying, rolling, wiping, dabbing, painting, rinsing, or dropping;

The method comprises administration by means of a pre-filled administration device as indicated herein;

The method comprises administration through a needle no larger than 20 gauge, preferably smaller than 20 gauge, and most preferably 23 gauge or smaller;

The method comprises a single administration every 7 to 360 days, preferably 7 to 120 days, for example 14 to 90 days;

The method comprises a single administration every 14 to 180 days, preferably around 90 days.

In combination with the features and preferred features indicated herein, the use(s) of the pre-formulations indicated herein in the manufacture of medicaments may have one or more of the following preferred features independently or in combination:

The use comprises the use of at least one formulation with one or more preferred features as indicated above;

The use comprises the manufacture of a medicament for administration of at least one formulation as indicated herein;

The use comprises the manufacture of a medicament for administration by means of a pre-filled administration device as indicated herein;

The use comprises the manufacture of a medicament for administration through a needle no larger than 20 gauge, preferably smaller than 20 gauge, and most preferably 23 gauge or smaller;

The use comprises the manufacture of a medicament for administration once every 7 to 360 days, preferably 7 to 120 days, for example 14 to 90 days.

In combination with the features and preferred features indicated herein, the pre filled devices of the invention may have one or more of the following preferred features independently or in combination:

They contain a preferred formulation as indicated herein;
They comprise a needle smaller than 20 gauge, preferably no larger than 23 gauge;

In combination with the features and preferred features indicated herein, the method(s) of treatment of the present invention may have one or more of the following preferred features independently or in combination:

The method comprises the administration of at least one formulation with one or more preferred features as indicated above;

The method is for the treatment of a condition selected from Cushing's disease, acromegaly, type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity, enterocutaneous and pancreaticocutaneous fistula, irritable bowel syndrome, inflammatory diseases, e.g. Grave's Disease, inflammatory bowel disease, psoriasis or rheumatoid arthritis, polycystic kidney disease, dumping syndrome, watery diarrhea syndrome, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding. T;

The method is for prophylaxis against at least one condition selected from Cushing's disease, acromegaly, type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity, enterocutaneous and pancreaticocutaneous fistula, irritable bowel syndrome, inflammatory diseases, e.g. Grave's Disease, inflammatory bowel disease, psoriasis or rheumatoid arthritis, polycystic kidney disease, dumping syndrome, watery diarrhea syndrome, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding.

The Invention will now be further illustrated by reference to the following non-limiting Examples and the attached Figures.

FIGURES

FIG. 1: Apparent absorbance (turbidity) of the aqueous phase measured at 600 nm for gels with the indicated lipid compositions (wt %) incubated in 0.1 wt % sodium taurocholate (NaTC). The gels were incubated at 37° C. for 6 hours with moderate shaking (150 rpm). See also Table 1 for composition details.

FIG. 2: X-ray diffraction patterns of fully hydrated DOPE/GDO mixtures in saline at 25, 37 and 42° C. between DOPE/GDO weight ratios of 75/25 and 35/65 as indicated in the figure. The relative diffraction peak positions indicate the liquid crystalline structure change from reversed hexagonal to reversed micellar cubic (space group Fd3m) when the GDO content is increased.

FIG. 3: X-ray diffraction patterns of fully hydrated DOPE/GDO (60/40 by weight) and DOPE/TOC (60/40 by weight) mixtures in saline at 25, 37 and 42° C. The relative diffraction peak positions indicate the same reversed micellar cubic (Fd3m) liquid crystalline structure within the temperature range investigated.

FIG. 4: X-ray diffraction patterns of fully hydrated (in saline (0.9% NaCl w/v)) DOPE/GDO (50/50 by weight) mixtures including octreotide at 25, 37 and 42° C. The octreotide concentration in the respective lipid formulation is indicated in the figure. The relative diffraction peak positions indicate the same reversed micellar cubic (Fd3m) liquid crystalline structure within the octreotide concentration and temperature range investigated.

FIG. 5: In vivo pharmacokinetic profile of octreotide (OCT) after subcutaneous administration in rats. Error bars denote standard deviation (n=6). Formulation compositions are provided in Example 10.

FIG. 6: In vivo pharmacokinetic profile of octreotide (OCT) after subcutaneous administration in rats. Error bars denote standard deviation (n=6). Formulation compositions are provided in Example 11.

FIG. 7: In vivo pharmacokinetic profile of octreotide (OCT) after subcutaneous administration in rats. Error bars denote standard deviation (n=6). Formulation compositions are provided in Example 12.

FIG. 8: A comparison of the mechanical robustness of liquid crystalline gels formed by DOPE/GDO and SPC/GDO mixtures in aqueous solution (PBS, pH 7.4). The following phospholipid/GDO weight ratios were investigated and compared: 70:30 (a), 65:35 (b), 60:40 (c), 55:45 (d) and 50:50 (e).

EXAMPLES

Materials

Soy phosphatidylcholine (SPC)—Lipoid S100 from Lipoid, Germany
Dioleoylphosphatidylethanolamine (DOPE)—Lipoid PE 18:1/18:1 from Lipoid, Germany
Glycerol dioleate (GDO)—Rylo DG19 Pharma from Danisco, Denmark
α-Tocopherol (TOC)—from DSM, Switzerland
Ethanol (EtOH) 99.5% Ph. Eur.—from Solveco, Sweden
Sodium taurocholate (NaTC)—from Sigma-Aldrich, Sweden
Octreotide hydrochloride (OCT)—from PolyPeptide Labs., USA
Pasireotide (SOM230) pamoate salt—from Novartis Pharma, Switzerland
Exenatide (EXT)—from Bachem, Switzerland
Propylene Glycol (PG)—from Dow, Germany
Water for Injection (WFI)—from B. Braun, Germany Example 1

Liquid Pre-Formulations Comprising Phospholipid and Diacylglycerol

Liquid pre-formulations (2 g) of phospholipid and diacylglycerol were prepared by weighing in the respective lipid and solvent components according to Table 1 in 3 mL (2R) vials followed by roller mixing at 40° C. until homogenous liquid solutions were obtained (<20 h). After cooling to room temperature, all formulations were observed to be homogenous liquids of low viscosity.

TABLE 1

Composition of liquid pre-formulations comprising phospholipid and diacylglycerol (wt %)

| Formulation# | SPC | DOPE | GDO | EtOH | Lipid composition (wt %) |
|---|---|---|---|---|---|
| 1 | 45 | — | 45 | 10 | SPC/GDO = 50/50 |
| 2 | 33.5 | 11.5 | 45 | 10 | SPC/DOPE/GDO = 37.5/12.5/50 |
| 3 | 22.5 | 22.5 | 45 | 10 | SPC/DOPE/GDO = 25/25/50 |
| 4 | 11 | 34 | 45 | 10 | SPC/DOPE/GDO = 12.5/37.5/50 |
| 5 | — | 45 | 45 | 10 | DOPE/GDO = 50/50 |
| 6 | 52.8 | — | 35.2 | 12 | SPC/GDO = 60/40 |
| 7 | 26.4 | 26.4 | 35.2 | 12 | SPC/DOPE/GDO = 30/30/40 |
| 8 | — | 52.8 | 35.2 | 12 | DOPE/GDO = 60/40 |
| 9 | — | 36 | 54 | 10 | DOPE/GDO = 40/60 |
| 10 | — | 59.5 | 25.5 | 15 | DOPE/GDO = 70/30 |

Example 2

Gelling of Pre-Formulations in Phosphate-Buffered Saline (PBS)

All liquid pre-formulations in Table 1 were subjected to a gelling test whereby 0.20 g of the respective formulation was injected into 5 mL of PBS (pH 7.4) in 6 mL (6R) injection glass vials using disposable 1 mL Luer-Lock syringes and 23 G needles. All formulations were easily injected using the 23 G needle size. The resulting gels were inspected visually after 1 h at room temperature and found to form coherent gels that could not be disrupted by mild shaking of the vials.

Example 3

Robustness of Lipid Gels in the Presence of Bile Salt

For long-term depot formulations and/or for per-oral formulations, a crucial property is related to the robustness of the gel towards erosion/fragmentation by endogenous surfactants and/or lipid-degrading enzymes. A way to study the robustness in vitro is to subject the lipid gels to a surfactant-rich aqueous environment and subsequently measure the increased turbidity (or apparent absorbance) of the aqueous phase resulting from surfactant-eroded lipid fragments. Such lipid fragments give rise to substantial increase in solution turbidity due to light scattering. Bile salts are often used as the surfactant of choice for studying formulation dissolution given their biological relevance and endogenous nature. Accordingly, gels (0.20 g) formed in PBS by the formulations given in Table 1 were placed in 5 mL of a 0.1 wt % sodium taurocholate (NaTC) solution in PBS. The resulting samples were thereafter transferred to an incubator held at 37° C. with 150 rpm rotating speed. After 6 hours, the samples were taken out from the incubator, turned up-side down twice, and the respective aqueous solution was transferred to a disposable semi-micro 1.5 mL cuvette for absorbance measurement. The (apparent) absorbance or turbidity was measured using a PerkinElmer Lambda 40 UV/Vis Spectrometer and air only was used for background correction. The results of the robustness study are shown in FIG. 1.

As is evident from FIG. 1, the more of the PE-component (DOPE) that is included in the formulation, the more robust the gel is towards surfactant-induced erosion. For example, by including 50% DOPE with respect to SPC (SPC/DOPE=50/50 wt/wt) (Formulation#3 and 7 in Table 1), a significant drop in turbidity is observed as a result of increased robustness towards surfactant-induced erosion. This effect is even more pronounced for formulations having an SPC/DOPE weight ratio of 25/75 (Formulation#4) and most pronounced for formulations comprising only the DOPE component in combination with GDO (Formulation#5, 8, 9 and 10 in Table 1). In fact, the aqueous solutions of the gels comprising only DOPE/GDO (Formulation#5, 8, 9 and 10 in Table 1) were completely transparent to the naked eye Example 4

Liquid Preformulations Comprising Phospholipid, Diacylglycerol, Low Viscosity Organic Solvent and Polar Solvent Liquid pre-formulations (1 g) of phospholipid and diacylglycerol were prepared as described in Example 1. After mixing, all formulations were observed to be homogenous liquids of low viscosity at room temperature. The compositions of the formulations are given in Table 2.

TABLE 2

Composition of liquid pre-formulations comprising phospholipid, diacylglycerol, low viscosity organic solvent and polar solvent (wt %)

| Formulation# | DOPE | GDO | EtOH | PG | WFI |
|---|---|---|---|---|---|
| 11 | 35.3 | 53.0 | 9.8 | 1.9 | — |
| 12 | 34.6 | 51.9 | 9.6 | 3.9 | — |
| 13 | 34.1 | 51.1 | 9.5 | 5.3 | — |
| 14 | 32.6 | 49.0 | 9.2 | 9.2 | — |
| 15 | 51.8 | 34.5 | 11.8 | — | 1.9 |
| 16 | 50.9 | 33.9 | 11.6 | — | 3.6 |
| 17 | 49.9 | 33.3 | 11.4 | — | 5.4 |
| 18 | 48.2 | 32.2 | 11.0 | — | 8.6 |

Example 5

Liquid Pre-Formulations Comprising Phospholipid and α-Tocopherol

Liquid pre-formulations (2 g) of phospholipid and α-tocopherol (TOC) are prepared by weighing in the respective lipid and solvent components according to Table 3 in 3 mL (2R) vials followed by roller mixing at 40° C. until homogenous liquid solutions are obtained (<20 h). After cooling to room temperature, all formulations are observed to be homogenous liquids of low viscosity.

TABLE 3

Composition of liquid pre-formulations comprising phospholipid and a-tocopherol (TOC) (wt %)

| Formulation# | SPC | DOPE | TOC | EtOH | Lipid composition (wt %) |
|---|---|---|---|---|---|
| 19 | 33.5 | 11.5 | 45 | 10 | SPC/DOPE/TOC = 37.5/12.5/50 |
| 20 | 22.5 | 22.5 | 45 | 10 | SPC/DOPE/TOC = 25/25/50 |
| 21 | 11 | 34 | 45 | 10 | SPC/DOPE/TOC = 12.5/37.5/50 |
| 22 | — | 45 | 45 | 10 | DOPE/TOC = 50/50 |
| 23 | 26.4 | 26.4 | 35.2 | 12 | SPC/DOPE/TOC = 30/30/40 |
| 24 | — | 52.8 | 35.2 | 12 | DOPE/TOC = 60/40 |
| 25 | — | 36 | 54 | 10 | DOPE/TOC = 40/60 |

Example 6

Liquid Crystalline Phase Structures from DOPE/GDO Mixtures in the Presence of Aqueous Phase Liquid pre-formulations (2 g) of DOPE and GDO were prepared by weighing the required amount of the respective lipid components in 3 mL (2R) vials followed by addition of EtOH at a total concentration of 10-15 wt %. The weight ratio of the lipids in the different samples was in the range DOPE:GDO=75:25-35:65. The samples were roller mixed at 40° C. until homogenous liquid solutions were obtained (<20 h). After cooling to room temperature, all formulations were observed to be homogenous liquids of low viscosity. The respective formulation (0.5 g) was thereafter injected into 5 mL of saline (0.9% w/v NaCl) in 6 mL (6R) injection glass vials using disposable 1 mL Luer-Lock syringes and 23 G needles. All formulations were easily injected using the 23 G needle size. The resulting gels were allowed to equilibrate on a roller mixer at ambient room temperature for 10 days before small angle X-ray scattering (SAXS) measurements.

Synchrotron SAXS measurements were performed at the I911 beamline at MAX-lab (Lund University, Sweden), using a Marresearch 165 mm CCD detector mounted on a Marresearch Desktop Beamline baseplate. The DOPE/GDO/saline liquid crystalline samples were mounted between kapton windows in a steel sample holder at the sample-to-detector distance of 1916.8 mm. Diffractograms were recorded at the indicated temperatures (FIG. 2) under high vacuum with a wavelength of 0.91 Å and the beam size of 0.25×0.25 mm (full width at the half maximum) at the sample. The exposure time for each sample was 3 min. The resulting CCD images were integrated and analysed using calibrated wavelengths and detector positions. The relative diffraction peak positions shown in FIG. 2 indicate that the liquid crystalline structure changes from reversed hexagonal ($H_2$) at high DOPE content to reversed micellar cubic ($I_2$, space group Fd3m) when the GDO content is increased.

Example 7

Liquid Crystalline Phase Structures from DOPE/TOC and DOPE/GDO Mixtures in the Presence of Aqueous Phase Liquid pre-formulations (2 g) of DOPE/GDO and DOPE/TOC were prepared by weighing the required amount of the respective lipid components in 3 mL (2R) vials followed by addition of EtOH at a total concentration of 10 wt %. The weight ratio of the lipids in the different samples was DOPE:GDO and DOPE:TOC=60:40. The samples were roller mixed at 40° C. until homogenous liquid solutions were obtained (<20 h). After cooling to room temperature, the formulations were observed to be homogenous liquids of low viscosity. The respective formulation (0.5 g) was thereafter injected into 5 mL of saline (0.9% w/v NaCl) in 6 mL (6R) injection glass vials using disposable 1 mL Luer-Lock syringes and 23 G needles. The formulations were easily injected using the 23 G needle size. The resulting gels were allowed to equilibrate on a roller mixer at ambient room temperature for 10 days before small angle X-ray scattering (SAXS) measurements.

Synchrotron SAXS measurements were performed as described in Example 6 and the results are shown in FIG. 3. The relative diffraction peak positions (FIG. 3) indicate the same reversed micellar cubic (Fd3m) liquid crystalline structure for both DOPE/GDO and DOPE/TOC (60/40 wt/wt) mixtures within the temperature range investigated.

Example 8

Liquid Crystalline Phase Structures from DOPE/GDO Preformulations Comprising Octreotide in the Presence of Aqueous Phase Liquid pre-formulations (5 g) comprising DOPE and GDO were prepared by weighing the required amount of the respective lipid component in 10 mL (10R) vials followed by addition of EtOH. The samples were roller mixed at 40° C. until homogenous liquid solutions were obtained (<20 h). After cooling to room temperature, octreotide hydrochloride (OCT) was added to the formulations at concentrations of 30 and 45 mg OCT free base/mL, respectively, followed by magnetic stirring until the formulations were observed to be homogenous liquids of low viscosity. The respective formulation (0.5 g) was thereafter injected into 5 mL of saline (0.9% w/v NaCl) in 6 mL (6R) injection glass vials using disposable 1 mL Luer-Lock syringes and 23 G needles. The formulations were easily injected using the 23 G needle size. The resulting gels were allowed to equilibrate on a roller mixer at ambient room temperature for 10 days before small angle X-ray scattering (SAXS) measurements. The final compositions of the preformulations comprising OCT are provided in Table 4.

TABLE 4

Composition of liquid pre-formulations comprising DOPE, GDO, EtOH and OCT (wt %)

| Formulation# | OCT | DOPE | GDO | EtOH | Comment |
|---|---|---|---|---|---|
| 26 | 3.62 | 43.19 | 43.19 | 10.00 | Corresponding to 30 mg octreotide free base per mL when corrected for peptide purity and content and formulation density. |
| 27 | 5.43 | 42.29 | 42.29 | 10.00 | Corresponding to 45 mg octreotide free base per mL when corrected for peptide purity and content and formulation density. |

Synchrotron SAXS measurements were performed as described in Example 6 and the results are shown in FIG. 4 where also the diffractogram for the DOPE/GDO mixture without octreotide is included. The relative diffraction peak positions indicate that the reversed micellar cubic (Fd3m) liquid crystalline structure observed for the DOPE/GDO mixture without the octreotide active agent is retained within the octreotide concentration and temperature range investigated.

Example 9

Formulation Comprising DOPE, GDO, EtOH, PG and Pasireotide (Pamoate Salt)

A liquid pre-formulation (2 g) comprising DOPE and GDO was prepared by weighing the required amount of the respective lipid component in 2 mL (2R) vials followed by addition of the required amount of EtOH and PG. The sample was roller mixed at 40° C. until a homogenous liquid solution was obtained (<20 h). After cooling to room temperature, pasireotide pamoate (or SOM230) was added to the formulation to give a final concentration of ca 30 mg/mL pasireotide (calculated as free base). The final sample composition is given in Table 5.

TABLE 5

Composition of liquid pre-formulation comprising DOPE, GDO, EtOH, PG and Pasireotide (wt %). The pasireotide concentration corresponds to approximately 30 mg pasireotide free base/mL.

| Formulation# | Pasireotide pamoate | DOPE | GDO | EtOH | PG |
|---|---|---|---|---|---|
| 28 | 4.77 | 38.50 | 38.76 | 8.58 | 9.39 |

Example 10

In Vivo Pharmacokinetic Study 1 of Formulations Comprising Octreotide

Liquid pre-formulations comprising DOPE/GDO and SPC/GDO were prepared by weighing the required amount of the respective lipid component in 15 mL (15R) vials followed by addition of EtOH. The samples were roller mixed at 40° C. until homogenous liquid solutions were obtained. The required amount of octreotide hydrochloride was weighed into a 10 mL (10R) glass vial followed by addition of the respective lipid/EtOH solution. The resulting formulations were roller mixed at ambient RT until homogenous liquid solutions were obtained. The respective formulation was thereafter sterile filtered under 2.5 bar nitrogen pressure using a sterile 0.2 micron PVDF membrane filter from Millipore. The batch size was 7 g and the final formulation compositions are provided in Table 6.

TABLE 6

Composition of liquid pre-formulations comprising phospholipid, GDO, co-solvent and OCT (wt %). The OCT concentration corresponds to 45 mg octreotide free base/mL.

| Formulation# | OCT | DOPE | SPC | GDO | EtOH |
|---|---|---|---|---|---|
| OCT-1 | 5.43 | 42.29 | — | 42.29 | 10.00 |
| OCT-2 | 5.43 | — | 42.29 | 42.29 | 10.00 |

The formulations in Table 6 were injected subcutaneously to male Sprague-Dawley rats at a dose volume of 0.6 mL/kg (27 mg octreotide free base/kg). Blood for pharmacokinetics were collected pre-dose, and 1 hour, 6 hours, 1 day, 2 days, 5 days, 8 days, 14 days, 21 days, 28 days and 35 days after dosing. Blood samples of 0.25 mL were collected by sublingual bleeding into EDTA-treated test tubes (Capiject 3T-MQK, Terumo Medical Corporation). The blood was placed on ice immediately after collection and centrifuged (approximately 1500×g, at 5° C. for 10 min) within 30 to 60 minutes. The plasma was transferred into properly labelled blue 1.5-mL propylene test tubes (Microcentrifuge tubes, Plastibrand, Buch & Holm) and stored below −70° C. until transportation on dry ice for analysis. The plasma samples were analysed with the ELISA kit S-1275 (Bachem/Peninsula Laboratories) "Octreotide—EIA Kit, Host: Rabbit, High Sensitivity", adapted for analysis of OCT in rat EDTA plasma.

The obtained PK profiles are shown in FIG. 5 demonstrating sustained release of OCT over at least 35 days for both formulations. Notably, the OCT-1 formulation comprising DOPE showed more stable plasma levels over time and in particular higher plasma levels from day 14 through day 35.

Example 11

In Vivo Pharmacokinetic Study 2 of Formulations Comprising Octreotide

Liquid pre-formulations (5 g) comprising phospholipid, GDO, co-solvents and octreotide were prepared as described in Example 10. The final formulation compositions are provided in Table 7.

TABLE 7

Composition of liquid pre-formulations comprising phospholipid, GDO, co-solvent and OCT (wt %)

| Formulation# | OCT | DOPE | SPC | GDO | EtOH | PG | Comment |
|---|---|---|---|---|---|---|---|
| OCT-1 | 5.43 | 42.29 | — | 42.29 | 10.00 | — | 45 mg OCT free base/mL |
| OCT-2 | 5.43 | — | 42.29 | 42.29 | 10.00 | — | 45 mg OCT free base/mL |
| OCT-3 | 2.40 | 43.80 | — | 43.80 | 10.00 | — | 20 mg OCT free base/mL |
| OCT-4 | 2.39 | — | 42.31 | 42.31 | 6.50 | 6.50 | 20 mg OCT free base/mL |

The formulations in Table 7 were injected subcutaneously to male Sprague-Dawley rats at a dose volume of 0.2 mL/kg (9 mg OCT free base/kg for OCT-1 and OCT-2 and 4 mg OCT free base/kg for OCT-3 and OCT-4). Blood for pharmacokinetics were collected pre-dose, and 1 hour, 6 hours, 1 day, 4 days, 6 days, 8 days, 11 days, 14 days, 18 days, 21 days, 25 days and 28 days after dosing. The sampling procedure and bioassay were as described in Example 10.

The obtained PK profiles are shown in FIG. 6 demonstrating sustained release of OCT over at least 28 days for all formulations. Notably, the OCT-1 and OCT-3 formulations comprising DOPE showed more stable plasma levels over time and in particular higher plasma levels from day 14 through day 28. The variability in measured plasma concentrations at longer times post injection (≥21 days) were also lower for the DOPE based formulations, especially pronounced for the OCT-3 formulation with 20 mg OCT free base/mL.

An interesting and noticeable finding in the study was that depots of the DOPE-based formulations were present at the injection site in all animals at termination whereas half or more of the animals receiving the SPC-based formulations showed complete clearance of the depot matrix. This indicates differences in lipid matrix in vivo degradation kinetics and supports the PK data at longer times post injection where the DOPE-based formulations showed higher and less variable plasma levels.

Example 12

In Vivo Pharmacokinetic Study 3 of Formulations Comprising Octreotide

Liquid pre-formulations (5 g) comprising phospholipid, GDO, co-solvents and octreotide were prepared as described in Example 10. The final formulation compositions are provided in Table 8.

TABLE 8

Composition of liquid pre-formulations comprising phospholipid, GDO, co-solvent and OCT (wt %). The OCT concentration corresponds to 20 mg OCT free base/mL.

| Formulation# | OCT | DOPE | SPC | GDO | EtOH |
|---|---|---|---|---|---|
| OCT-3 | 2.40 | 43.80 | — | 43.80 | 10.00 |
| OCT-5 | 2.39 | 35.04 | — | 52.57 | 10.00 |
| OCT-6 | 2.39 | 52.57 | — | 35.04 | 10.00 |
| OCT-7 | 2.39 | 39.43 | 4.37 | 43.81 | 10.00 |
| OCT-8 | 2.39 | 35.05 | 8.75 | 43.81 | 10.00 |

The formulations in Table 8 were injected subcutaneously to male Sprague-Dawley rats at a dose volume of 0.2 mL/kg (4 mg OCT free base/kg). Blood for pharmacokinetics were collected pre-dose, and 1 hour, 6 hours, 1 day, 4 days, 6 days, 8 days, 12 days, 14 days, 19 days, 21 days and 28 days after dosing. The sampling procedure and bioassay were as described in Example 10.

The obtained PK profiles are shown in FIG. 7 demonstrating sustained release of OCT over at least 28 days for all formulations. A higher initial release and lower plasma levels of OCT were observed for the OCT-5 formulation whereas the plasma profiles were similar for the other formulations.

Example 13

Mechanical Robustness of Liquid Crystals Formed by DOPE/GDO and SPC/GDO Mixtures in Aqueous Solution Liquid pre-formulations (1 g) of DOPE/GDO and SPC/GDO mixtures were prepared by weighing the required amount of the respective lipid components in 3 mL (2R) vials followed by addition of EtOH at a total concentration of 10 wt %. The weight ratio of the lipids in the different samples was in the range DOPE:GDO=70:30-50:50 and SPC:GDO=70:30-50:50. The samples were roller mixed at 40° C. until homogenous liquid solutions were obtained (<20 h). After cooling to room temperature, the formulations were observed to be homogenous liquids of low viscosity. The respective formulation (0.5 g) was thereafter injected into 5 mL of phosphate buffered saline (pH 7.4) in 10 mL (10R) injection glass vials using disposable 1 mL Luer-Lock syringes and 23 G needles. The formulations were easily injected using the 23 G needle size. The resulting gels were allowed to equilibrate on a mechanical mixing table at 37° C. and 150 rpm for 20 days before robustness measurements.

The liquid crystalline robustness measurements were performed by using TA.XT plus Texture Analyzer (Stable Micro Systems Ltd., UK) equipped with a 2 mm thick stainless needle. Force vs. distance dependencies were registered by penetrating the needle about 4 mm into the liquid crystalline gels at a speed of 0.5 mm/s. The higher the force required to penetrate the needle, the higher the mechanical resistance of the gel.

The results are shown in FIG. 8 showing in all cases that the DOPE-based liquid crystalline (LC) gels are significantly more mechanically robust compared to the SPC-based LC gels. This result is in line with the higher resistance towards surfactant-induced erosion as exemplified in Example 1. The higher mechanical robustness of the DOPE-based formulations in comparison to SPC-based formulations may also be one reason for the difference in in vivo performance between the formulation types as described in Examples 10-12.

The invention claimed is:

1. A pre-formulation comprising a low viscosity, non-liquid crystalline, mixture of:
   a. 25-55 wt. % of at least one diacyl glycerol and/or at least one tocopherol;
   b. 25-55 wt. % of at least one phospholipid component having
      i. polar head groups comprising more than 50% phosphatidyl ethanolamine, and
      ii. two acyl chains each independently having 16 to 20 carbons wherein at least one acyl chain has at least one unsaturation in the carbon chain, and there are no more than four unsaturations over two carbon chains;
   c. 5-25 wt. % of at least one biocompatible, oxygen containing, low viscosity organic solvent;
   wherein 0.1-10 wt. % of at least one peptide active agent comprising at least one somatostatin receptor agonist is dissolved or dispersed in the low viscosity mixture;
   wherein the pre-formulation has a viscosity of 0.1 to 5000 mPas;
   and wherein the pre-formulation forms, or is capable of forming, at least one non-lamellar liquid crystalline phase structure upon contact with an aqueous fluid.

2. A pre-formulation as claimed in claim 1 wherein said at least one peptide active agent is a constrained peptide of 6-10 α-amino acids or salts thereof.

3. A pre-formulation as claimed in claim 1 wherein said peptide active agent is a chloride, an acetate, a pamoate or a tartrate salt.

4. A pre-formulation as claimed in claim 1 wherein said peptide active agent is pasireotide, octreotide or a salt thereof.

5. A pre-formulation as claimed in claim 1 wherein said pre-formulation delivers a peptide active agent dosage in the range of 5 to 150 mg/ml.

6. A pre-formulation as claimed in claim 1 wherein said liquid crystalline phase structure is a reversed hexagonal phase structure or a reversed cubic phase structure or mixtures thereof.

7. A pre-formulation as claimed in claim 1 wherein the non-polar tail groups of component a) each independently consist essentially of unsaturated C18 groups.

8. A pre-formulation as claimed in claim 1 wherein component a) consists essentially of at least one tocopherol.

9. A pre-formulation as claimed in claim 1 wherein component a) consists essentially of a mixture of GDO and tocopherol.

10. A pre-formulation as claimed in claim 1 wherein component b) is selected from phosphatidyl ethanolamines, or mixtures of phosphatidyl ethanolamines with at least one selected from phosphatidyl cholines, phosphatidyl inositols, and sphingomyelins.

11. A pre-formulation as claimed in claim 1 wherein said phospholipid component b) comprises more than 50% PE.

12. A pre-formulation as claimed in claim 1 wherein the phospholipid component b) further comprises at least one phospholipid having
   i. polar head groups comprising at least 90% phosphatidyl choline, and
   ii. two acyl chains each independently having 16 to 20 carbons wherein at least one acyl chain has at least one unsaturation in the carbon chain, and there are no more than four unsaturations over two carbon chains.

13. A pre-formulation as claimed in claim 1 wherein the phospholipid component b) comprises at least 10% PC, SPC, DOPC or mixtures thereof.

14. A pre-formulation as claimed in claim 1 having a molecular solution, $L_2$ and/or $L_3$ phase structure.

15. A pre-formulation as claimed in claim 1 having a ratio of a) to b) of between 80:20 and 5:95 by weight.

16. A pre-formulation as claimed in claim 1 wherein component c) is selected from an alcohol, a ketone, an ester, an ether, an amide, a sulphoxide and mixtures thereof.

17. A pre-formulation as claimed in claim 1 wherein component c) comprises ethanol, NMP or mixtures thereof.

18. A pre-formulation as claimed in claim 1 additionally comprising up to 10% by weight of a)+b) of a charged amphiphile.

19. A pre-formulation as claimed in claim 1 further comprising:
   d. 1 to 20 wt. % of at least one polar solvent by weight of components a)+b)+c)+d), preferably wherein said polar solvent has a dielectric constant of at least 28 measured at 25° C.

20. A pre-formulation as claimed in claim 19 wherein component d) comprises water, propylene glycol or mixtures thereof.

21. A pre-formulation as claimed in claim 19 where component d) comprises at least 2% water.

22. A pre-formulation as claimed in claim 19 wherein component d) is present at a level of 1.2 to 20% by weight.

23. A pre-formulation as claimed in claim 19 wherein component c) comprises at least one biocompatible, organic, mono-alcoholic solvent.

24. A pre-formulation as claimed in claim 19 wherein component c) comprises a solvent selected from the group consisting of ethanol, propanol, isopropanol or mixtures thereof, DMSO, NMP or mixtures of NMP and ethanol.

25. A pre-formulation as claimed in claim 19 wherein components c) and d) combined are present at a total level less than or equal 30% by weight.

26. A pre-formulation as claimed in claim 1 which is administrable by injection, spraying, dipping, rinsing, application from a pad or ball roller, painting, dropping, aerosol spraying or pump spraying.

27. An injectable pre-formulation as claimed in claim 1 which forms a depot providing continuous release of active agent for at least two weeks, wherein said active agent comprises at least one selected from octreotide or pasireotide.

28. A process for the formation of a pre-formulation according to claim 1 suitable for the administration of a peptide active agent comprising at least one somatostatin receptor agonist to a subject, said process comprising forming a non-liquid crystalline, low viscosity mixture of
   a. 25-55 wt. % of at least one diacyl glycerol and/or at least one tocopherol;
   b. 25-55 wt. % of at least one phospholipid component having
      i. polar head groups comprising more than 50% phosphatidyl ethanolamine, and
      ii. two acyl chains each independently having 16 to 20 carbons wherein at least one acyl chain has at least one unsaturation in the carbon chain, and there are no more than four unsaturations over two carbon chains;
   c. 5-25 wt. % of at least one biocompatible, oxygen containing, low viscosity organic solvent;
   and dissolving or dispersing 0.1-10 wt. % of at least one peptide active agent comprising at least one somatostatin receptor agonist in the low viscosity mixture, or in at least one of components a, b or c prior to forming the low viscosity mixture.

29. A process as claimed in claim 28 wherein said at least one peptide active agent is a constrained peptide of 6-10 α-amino acids.

30. A method of treatment or prophylaxis of a human or non-human animal subject comprising administration of a pre-formulation as claim 1, wherein the condition to be treated is selected from Cushing's disease, acromegaly, type I diabetes mellitus or type II diabetes mellitus, metabolic disorders related to insulin or glucagon release, enterocutaneous and pancreaticocutaneous fistula, irritable bowel syndrome, inflammatory diseases, polycystic kidney disease, dumping syndrome, watery diarrhea syndrome, AIDS-related diarrhea, chemotherapy-induced diarrhea, acute or chronic pancreatitis and gastrointestinal hormone secreting tumors, lymphocyte malignancies and gastrointestinal bleeding;
   or wherein the condition for prophylaxis against is Cushing's disease, acromegaly, type I diabetes mellitus or type II diabetes mellitus, metabolic disorders related to insulin or glucagon release, enterocutaneous and pancreaticocutaneous fistula, irritable bowel syndrome, inflammatory diseases, polycystic kidney disease, dumping syndrome, watery diarrhea syndrome, AIDS-related diarrhea, chemotherapy-induced diarrhea, acute or chronic pancreatitis and gastrointestinal hormone secreting tumors, lymphocyte malignancies and gastrointestinal bleeding.

31. A pre-filled administration device containing a pre-formulation as claimed in claim 1.

32. The device as claimed in claim 31 being a syringe or syringe barrel, a needle-less injector, a multi- or single-use injector, a cartridge or a vial.

33. The device of claim 31 containing a single dose of 1 to 200 mg, of a peptide active agent comprising at least one somatostatin receptor agonist.

34. The device of claim 31 containing a peptide active agent comprising at least one somatostatin receptor agonist at around 0.2 to 4 mg per day between scheduled administrations.

35. The device of claim 31 containing a total volume for administration of no more than 5 ml.

36. A kit comprising an administration device as claimed in claim 31.

* * * * *